(12) United States Patent
Manosroi et al.

(10) Patent No.: US 6,955,910 B2
(45) Date of Patent: Oct. 18, 2005

(54) METHOD FOR LARGE SCALE PRODUCTION OF RECOMBINANT DNA-DERIVED TPA OR K2S MOLECULES

(75) Inventors: Jiradej Manosroi, Chiang Mai (TH); Aranya Manosroi, Chiang Mai (TH); Chatchai Tayapiwatana, BKK (TH); Friedrich Goetz, Tuebingen (DE); Rolf-Guenther Werner, Biberach (DE)

(73) Assignee: Boehringer Ingelheim International GmbH (DE)

( * ) Notice: Subject to any disclaimer, the term of this patent is extended or adjusted under 35 U.S.C. 154(b) by 124 days.

(21) Appl. No.: 09/987,455

(22) Filed: Nov. 14, 2001

(65) Prior Publication Data

US 2003/0049729 A1 Mar. 13, 2003

Related U.S. Application Data

(60) Provisional application No. 60/268,574, filed on Feb. 15, 2001.

(30) Foreign Application Priority Data

Nov. 14, 2000 (GB) .............................. 0027779

(51) Int. Cl.$^7$ ............................ C12N 1/21; C07H 21/04
(52) U.S. Cl. ................................ 435/252.33; 435/91.1; 435/320.1; 536/23.1; 536/23.2
(58) Field of Search ................................ 435/219, 226, 435/252.3, 252.33, 320.1, 69.1, 216, 91.1; 536/23.2, 23.1, 23.6; 530/350

(56) References Cited

U.S. PATENT DOCUMENTS

| | | | | |
|---|---|---|---|---|
| 5,840,533 A | * | 11/1998 | Niwa et al. ................. | 435/69.1 |
| 6,027,888 A | * | 2/2000 | Georgiou et al. .............. | 435/6 |
| 6,083,715 A | | 7/2000 | Georgiou et al. .......... | 435/69.1 |
| 2003/0013150 A1 | | 1/2003 | Manosroi et al. | |
| 2003/0049729 A1 | | 3/2003 | Manosroi et al. | |

FOREIGN PATENT DOCUMENTS

| | | |
|---|---|---|
| EP | 0 302 456 A1 | 2/1989 |
| EP | 0 357 391 A2 | 3/1990 |
| EP | 0 467 676 A2 | 1/1992 |
| EP | 1 048 732 A1 | 11/2000 |
| EP | 1 077 263 A1 | 2/2001 |
| WO | WO 97/38123 A1 | 10/1997 |
| WO | WO 98/54199 A1 | 12/1998 |
| WO | WO 02/40650 | 5/2002 |
| WO | WO 02/40696 | 5/2002 |

OTHER PUBLICATIONS

Hu, S.Z., et al., "Minibody: A Novel Engineered Anti–Carcinoembryonic Antigen Antibody Fragment (Single–chain Fv–CH$_3$) which exhibits rapid, high–level targeting of xenografts," *Cancer Res.* 56:3055–3061, American Association for Cancer Research (1996).

Huston, J.S., et al., "Protein engineering of antibody binding sites: Recovery of specific activity in an anti–digoxin single–chain Fv analogue produced in *Escherichia coli*," *Proc. Natl. Acad. Sci. USA* 85:5879–5883, National Academy of Sciences (1988).

Kortt, A.A., et al., "Single–chain Fv fragments of anti–neuraminidase antibody NC10 containing five– and ten–residue linkers form dimers and with zero–residue linker a trimer," *Protein Eng.* 10:423–433, Oxford University Press (1997).

Lovejoy, B., et al., "Crystal Structure of a Synthetic Triple–Stranded α–Helical Bundle," *Science* 259:1288–1293, American Association for the Advancement of Science (1993).

NCBI Entrez, Genbank report, Accession No. AF268281, from Rader, C., and Barbas, C. F. III (Oct. 2000).

Pack, P., et al., "Improved Bivalent Miniantibodies, with Identical Avidity as Whole Antibodies, Produced by High Cell Density Fermentation of *Escherichia coli*," *Bio/Technology* 11:1271–1277, Nature Publishing Co. (1993).

Pack, P., et al., "Tetravalent Miniantibodies with High Avidity Assembling in *Escherichia coli*," *J. Mol. Biol.* 246:28–34, Academic Press Ltd. (1995).

Perisic, O., et al., "Crystal structure of a diabody, a bivalent antibody fragment," *Structure* 2:1217–1226, Current Biology Ltd. (1994).

Sivaprasadarao, A. and Findlay, J.B., "Expression of functional human–retinol–binding protein in *Escherichia coli* using a secretion vector," *Biochem. J.* 296:209–215, Biochemical Society/Portland Press (1993).

NCBI Entrez, GenBank Report, Accession No. E02814, from Habuka, N., et al. (1991).

Barbas, C.F. III and J. Wagner, "Synthetic Human Antibodies: Selecting and Evolving Functional Proteins," *Methods* 8:94–103, Academic Press (1995).

Bennett, W.F. et al., "High Resolution Analysis of Functional Determinants on Human Tissue–type Plasminogen Activator," *J. Biol. Chem.* 266:5191–5201, The American Society for Biochemistry and Molecular Biology, Inc. (1991).

(Continued)

*Primary Examiner*—Nashaat T. Nashed
(74) *Attorney, Agent, or Firm*—Sterne, Kessler, Goldstein & Fox P.L.L.C.

(57) ABSTRACT

The invention belongs to the field of thrombolysis and of tissue plasminogen activator (tPA) derivative production in prokaryotic cells. The invention relates to methods for the production of a recombinant DNA-derived tPA, a variant therof or a (Kringle 2 Serine) K2S molecule or a variant therof in prokaryotic cells, wherein the tPA or K2S or variant is secreted extracellularly as an active and correctly folded protein, and the prokaryotic cell contains and expresses a vector comprising the DNA coding for the tPA or K2S or variant operably linked to the DNA coding for the signal peptide OmpA. The invention further relates to specific K2S derivatives obtainable by the method. The invention further relates to the DNA molecules and the use of the DNA molecules in the methods.

19 Claims, 15 Drawing Sheets

OTHER PUBLICATIONS

Figure 1:
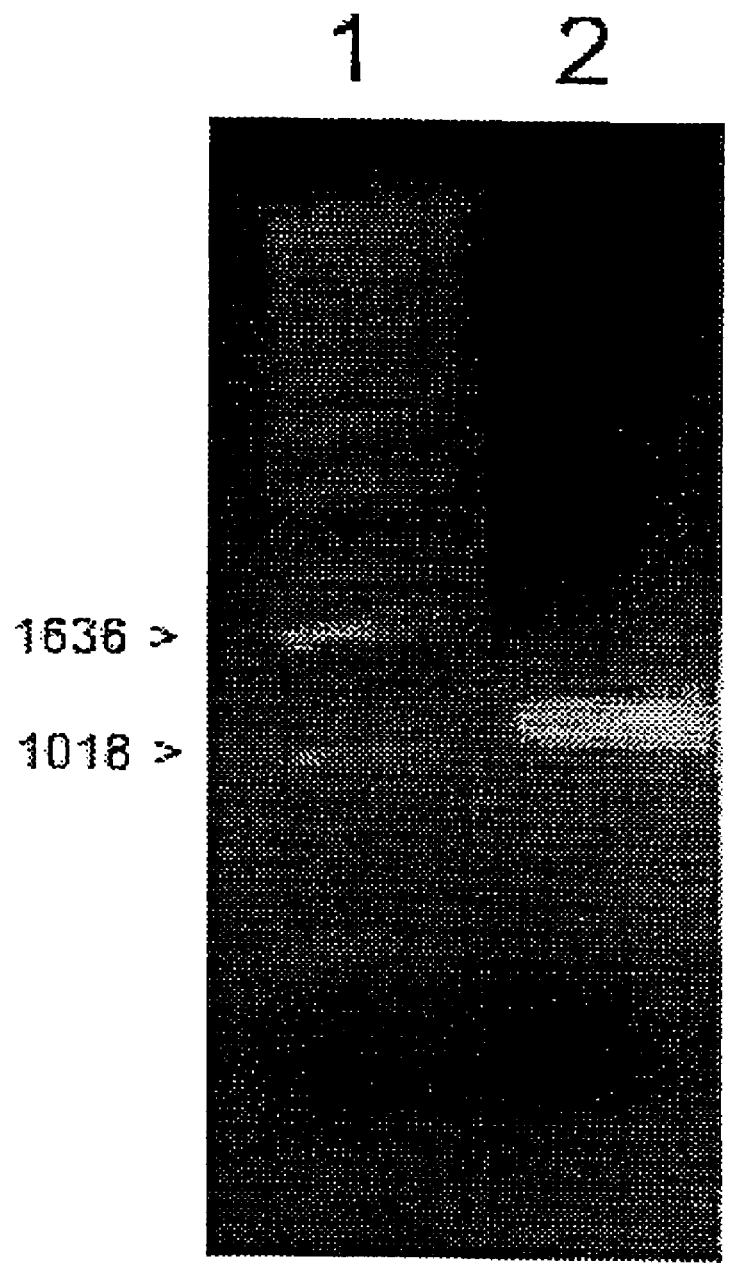

Betton, J.-M. et al., "Degradation versus Aggregation of Misfolded Maltose–binding Protein in the Periplasm of *Escherichia coli*," *J. Biol. Chem.* 273:8897–8902, The American Society for Biochemistry and Molecular Biology, Inc. (1998).

Allen, S. et al., "Intracellular Folding of Tissue–type Plasminogen Activator. Effects of Disulfide Bond Formation on N–linked Glycosylation and Secretion," *J. Biol. Chem.* 270:4797–4804, The American Society for Biochemistry and Molecular Biology, Inc. (1995).

Ames, G.F.-L. et al., "Simple, Rapid, and Quantitative Release of Periplasmic Proteins by Chloroform," *J. Bacteriol.* 160:1181–1183, American Society for Microbiology (1984).

Barbas, C.F. III et al., "Assembly of combinatorial antibody libraries on phage surfaces: The gene III site," *Proc. Natl. Acad. Sci. U.S.A.* 88:7978–7982, The National Academy of Sciences of the U.S.A. (1991).

Camiolo, S.M. et al., "Fibrinogenolysis and Fibrinolysis with Tissue Plasminogen Activator, Urokinase, Streptokinase–Activated Human Globulin and Plasmin," *Proc. Soc. Exp. Biol. Med.* 138:277–280, Academic Press (1971).

Cartwright, T., "Production of tPA from Animal Cell Cultures," In *Animal Cell Biotechnology*, vol. 5, R.E. Spier and J.B. Griffiths (eds.), Academic Press, N.Y. p. 217–245 (1992).

Curry, K.A. et al., "*Escherichia coli* Expression and Processing of Human Interleukin–1β Fused to Signal Peptides," *DNA Cell Biol.* 9:167–175, Mary Ann Liebert, Inc. (1990).

Datar, R.V. et al., "Process Economics of Animal Cell and Bacterial Fermentations: A Case Study Analysis of Tissue Plasminogen Activator," *Bio/Technology* 11:349–357, Nature Publishing Company (1993).

Denèfle, P. et al., "Heterologous protein export in *Escherichia coli*: influence of bacterial signal peptides on the export of human interleukin 1β," *Gene* 85:499–510, Elsevier Science Publishers B.V. (Biomedical Division) (1989).

Griffiths, J.B. and A. Electricwala, "Production of Tissue Plasminogen Activators from Animal Cells," *Adv. Biochem. Eng. Biotechnol.* 34:147–166, Springer–Verlag (1987).

Harris, T.J.R. et al., "Cloning of cDNA Coding for Human Tissue–type Plasminogen Activator and its Expression in *Escherichia coli*," *Mol. Biol. Med.* 3:279–292, Academic Press Inc. (1986).

Heussen, C. and E.B. Dowdle, "Electrophoretic Analysis of Plasminogen Activators in Polyacrylamide Gels Containing Sodium Dodecyl Sulfate and Copolymerized Substrates," *Anal. Biochem.* 102:196–202, Academic Press, Inc. (1980).

Heussen, C. et al., "Purification of Human Tissue Plasminogen Activator with Erythrina Trysin Inhibitor," *J. Biol. Chem.* 259:11635–11638, The American Society of Biological Chemists, Inc. (1984).

Hu, C.-K. et al., "Tissue–Type Plasminogen Activator Domain–Deletion Mutant BM 06.022: Modular Stability, Inhibitor Binding, and Activation Cleavage," *Biochemistry* 33:11760–11766, American Chemical Society (1994).

Kipriyanov, S.M. et al., "High level production of soluble single chain antibodies in small–scale *Escherichia coli* cultures," *J. Immunol. Methods* 200:69–77, Elsevier Science B.V. (1997).

Ko, J.H. et al., "High–level Expression and Secretion of Streptokinase in *Escherichia coli*," *Biotechnol. Lett.* 17:1019–1024, Chapman & Hall (1995).

Kouzuma, Y. et al., "The Tissue–Type Plasminogen Activator Inhibitor ETIa from *Erythrina variegata*: Structural Basis for the Inhibitory Activity by Cloning, Expression, and Mutagenesis of the cDNA Encoding ETIa," *J. Biochem. (Tokyo)* 121:456–463, The Japanese Biochemical Society (1997).

Lasters, I. et al., "Enzymatic properties of phage–displayed fragments of human plasminogen," *Eur. J. Biochem.* 244:946–952, Springer International on behalf of the Federation of European Biochemical Societies (1997).

Lobel, L.I. et al., "Filamentous Phage Displaying the Extracellular Domain of the hLH/CG Receptor Bind hCG Specifically," *Endocrinology* 138:1232–1239, The Endocrine Society (1997).

Lubiniecki, A. et al., "Selected Strategies for Manufacture and Control of Recombinant Tissue Plasminogen Activator Prepared from Cell Cultures," In *Advances In Animal Cell Biology and Technology for Bioprocesses*, R.E. Spier et al., (ed.), Butterworth & Co., London, p. 442–451 (1989).

Lucic, M.R. et al., "Secretion in *Escherichia coli* and phage—display of recombinant insulin–like growth factor binding protein–2," *J. Biotechnol.* 61:95–108, Elsevier Science B.V. (1998).

Martin, U. et al., "Properties of a novel plasminogen activator (BM 06.022) produced in *Escherichia coli*," *Z. Kardiol.* 79:167–170, Steinkopff Verlag Darmstadt (1990).

Obukowicz, M.G. et al., "Secretion of Active Kringle–2–Serine Protease in *Escherichia coli*," *Biochemistry* 29:9737–9745, American Chemical Society (1990).

Parmley, S.F. and G.P. Smith, "Antibody–selectable filamentous fd phage vectors: affinity purification of target genes," *Gene* 73:305–318, Elsevier Science Publishers B.V. (1988).

Pennica, D. et al., "Cloning and epxression of human tissue–type plasminogen activator cDNA in *E. coli*," *Nature* 301:214–221, Macmillan Journals Ltd. (1983).

Rippmann, J.F. et al., "Procaryotic Expression of Single–Chain Variable–Fragment (scFv) Antibodies: Secretion in L–Form Cells of *Proteus mirabilis* Leads to Active Product and Overcomes the Limitations of Periplasmic Expression in *Escherichia coli*," *Appl. Environ. Microbiol.* 64:4862–4869, American Society for Microbiology (1998).

Saito, Y. et al., "Production and Characterization of a Novel Tissue–Type Plasminogen Activator Derivative in *Escherichia coli*," *Biotechnol. Prog.* 10:472–479, American Chemical Society and American Institute of Chemical Engineers (1994).

Sarmientos, P. et al., "Synthesis and Purification of Active Human Tissue Plasminogen Activator from *Escherichia coli*," *Bio/Technology* 7:495–501, Nature Publishing Company (1989).

Scherrer, S. et al., "Periplasmic aggregation limits the proteolytic maturation of the *Escherichia coli* Penicillin G amidase precursor polypeptide," *Appl. Microbiol. Biotechnol.* 42:85–91, Springer–Verlag (1994).

Soeda, S. et al., "Rapid and High–Yield Purification of Porcine Heart Tissue–Type Plasminogen Activator by Heparin–Sepharose Choromatography," *Life Sci.* 39:1317–1324, Pergamon Journals Ltd. (1986).

Szarka, S.J. et al., "Staphylokinase as a Plasminogen Activator Component in Recombinant Fusion Proteins," *Appl. Environ. Microbiol.* 65:506–513, American Society for Microbiology (Feb. 1999).

Waldenström, M. et al., "Synthesis and secretion of a fibrinolytically active tissue–type plasminogen activator variant in *Escherichia coli*," *Gene* 99:243–248 (1991).

Wan, E.W.–M., "TolAIII Co–overexpression Facilitates the Recovery of Periplasmic Recombinant Proteins into the Growth Medium of *Escherichia coli*," *Protein Expr. Purif.* 14:13–22, Academic Press (1998).

Zacharias, U. et al., "Characterization of Human Tissue–type Plasminogen Activator with Monoclonal Antibodies: Mapping of Epitopes and Binding Sites for Fibrin and Lysine," *Thromb. Haemost.* 67:88–94, F.K. Schattauer Verlagsgesellschaft mbH (1992).

Andris–Widhopf, J., et al., "Methods for the generation of chicken monoclonal antibody fragments by phage display," *J. Immunol. Meth.* 242:159–181, Elsevier Science B.V. (Aug. 2000).

Cleary, S., et al., "Purification and Characterization of Tissue Plasminogen Activator Kringle–2 Domain Expressed in *Escherichia coli*," *Biochem.* 28:1884–1891, American Chemical Society (1989).

Hua, Z.–C., et al., "Synthesis and Expression of a Gene From Kringle–2 Domain of Tissue Plasminogen Activator in *E. coli*," *Sci. China (Series B)* 37:667–676, Chinese Acadeny of Sciences: Science Press (1994).

Manosroi, J., et al., "Secretion of Active Recombinant Human; Tissue Plasminogen Activator Derivatives in *Escherichia coli*," *Appl. Envir. Microbiol.* 67:2657–2664, American Society for Microbiology (Jun. 2001).

Qiu, J., et al., "Expression of Active Human Tissue–Type Plasminogen Activator in *Escherichia coli*," *Appl. Envir. Microbiol.* 64:4891–4896, American Society for Microbiology (1998).

Weiner, M.P., and G.L. Costa, "Rapid PCR Site–directed Mutagenesis," *PCR Meth. Appl.* 4:S131–S136, Cold Spring Harbor Laboratory Pres (1994).

Weiner, M.P., et al., "Site–directed mutagenesis of double–stranded DNA by the polymerase chain reaction," *Gene* 151:119–123, Elsevier Science B.V. (1994).

International Search Report for International Application No. PCT/EP01/12857, mailed May 10, 2002.

International Search Report for International Application No. PCT/EP01/12920, mailed Jun. 11, 2002.

Dialog File 351, Accession No. 13502244, Derwent WPI English language abstract for EP 1 048 732 A1 (Document AL2).

Dialog File 351, Accession No. 2001–204356/200121, Derwent WPI English language abstract for EP 1 077 263 A1 (Document AM2).

Pending Non–Provisional U.S. Appl. No. 09/987,457, Manosroi et al., filed Nov. 14, 2001 (Not Published).

* cited by examiner

SEQUENCE LISTING

<160> NUMBER OF SEQ ID NOS: 26

<210> SEQ ID NO 1
<211> LENGTH: 18
<212> TYPE: DNA

<213> ORGANISM: Artificial Sequence
<220> FEATURE:
<223> OTHER INFORMATION: Description of Artificial Sequence: coding
      sequence of N-terminal part of K2S protein

<400> SEQUENCE: 1
tctgagggaa acagtgac                                                    18

<210> SEQ ID NO 2
<211> LENGTH: 1128
<212> TYPE: DNA
<213> ORGANISM: Artificial Sequence
<220> FEATURE:
<223> OTHER INFORMATION: Description of Artificial Sequence: coding
      sequence for OmpA-K2S fusion protein

<400> SEQUENCE: 2
atgaaaaaga cagctatcgc gattgcagtg gcactggctg gtttcgctac cgtggcccag      60
gcggcctctg agggaaacag tgactgctac tttgggaatg ggtcagccta ccgtggcacg     120
cacagcctca ccgagtcggg tgcctcctgc ctcccgtgga attccatgat cctgataggc     180
aaggtttaca gcacagaa ccccagtgcc caggcactgg gcctgggcaa acataattac        240
tgccggaatc ctgatgggga tgccaagccc tggtgccacg tgctgaagaa ccgcaggctg     300
acgtgggagt actgtgatgt gccctcctgc tccacctgcg gcctgagaca gtacagccag     360
cctcagtttc gcatcaaagg agggctcttc gccgacatcg cctcccaccc ctggcaggct     420
gccatctttg ccaagcacag gaggtcgccc ggagagcggt tcctgtgcgg ggcatactc      480 atcagctcct gctggattct ctctgccgcc cactgcttcc aggagaggtt ccgccccac      540 cacctgacgg tgatcttggg cagaacatac cgggtggtcc ctggcgagga ggagcagaaa     600
tttgaagtcg aaaaatacat tgtccataag gaattcgatg atgacactta cgacaatgac     660
attgcgctgc tgcagctgaa atcggattcg tcccgctgtg cccaggagag cagcgtggtc     720
cgcactgtgt gccttccccc ggcggacctg cagctgccgg actggacgga gtgtgagctc     780
tccggctacg gcaagcatga ggccttgtct cctttctatt cggagcggct gaaggaggct     840
catgtcagac tgtacccatc agccgctgc acatcacaac atttacttaa cagaacagtc     900
accgacaaca tgctgtgtgc tggagacact cggagcggcg ggccccaggc aaacttgcac     960
gacgcctgcc agggcgattc ggggaggcccc ctggtgtgtc tgaacgatgg ccgcatgact    1020
ttggtgggca tcatcagctg gggcctgggc tgtggacaga aggatgtccc gggtgtgtac    1080
acaaaggtta ccaactacct agactggatt cgtgacaaca tgcgaccg                  1128

<210> SEQ ID NO 3
<211> LENGTH: 66
<212> TYPE: DNA
<213> ORGANISM: Escherichia coli

<400> SEQUENCE: 3
atgaaaaaga cagctatcgc gattgcagtg gcactggctg gtttcgctac cgtggcccag      60
gcggcc                                                                66

<210> SEQ ID NO 4
<211> LENGTH: 1065
<212> TYPE: DNA
<213> ORGANISM: Artificial Sequence
<220> FEATURE:
<223> OTHER INFORMATION: Description of Artificial Sequence: coding
      sequence for K2S protein -continued

```
<400> SEQUENCE: 4
tctgagggaa acagtgactg ctactttggg aatgggtcag cctaccgtgg cacgcacagc      60
ctcaccgagt cgggtgcctc ctgcctcccg tggaattcca tgatcctgat aggcaaggtt     120
tacacagcac agaaccccag tgcccaggca ctgggcctgg gcaaacataa ttactgccgg     180
aatcctgatg gggatgccaa gccctggtgc acgtgctgaa gaaccgcag gctgacgtgg      240 gagtactgtg atgtgccctc ctgctccacc tgcggcctga cagtacag ccagcctcag       300 tttcgcatca aggagggct cttcgccgac atcgcctccc accctggca ggctgccatc      360 tttgccaagc acaggaggtc gccccggagag cggttcctgt gcgggggcat actcatcagc    420
tcctgctgga ttctctctgc cgcccactgc ttccaggaga ggtttccgcc ccaccacctg     480
acggtgatct gggcagaac ataccgggtg gtccctggcg aggaggagca gaaatttgaa      540
gtcgaaaaat acattgtcca taaggaattc gatgatgaca cttacgacaa tgacattgcg     600
ctgctgcagc tgaaatcgga ttcgtcccgc tgtgcccagg agagcagcgt ggtccgcact     660
gtgtgccttc cccggcgga cctgcagctg ccggactgga cggagtgtga gctctccggc     720
tacggcaagc atgaggcctt gtctcctttc tattcggagc ggctgaagga ggctcatgtc     780
agactgtacc catccagccg ctgcacatca aacatttac ttaacagaac agtcaccgac      840
aacatgctgt gtgctggaga cactcggagc ggcgggcccc aggcaaactt gcacgacgcc     900
tgccagggcg attcggagg ccccctggtg tgtctgaacg atggccgcat gactttggtg      960
ggcatcatca gctggggcct gggctgtgga cagaaggatg tcccgggtgt gtacacaaag    1020
gttaccaact acctagactg gattcgtgac aacatgcgac cgtga                    1065
```

<210> SEQ ID NO 5
<211> LENGTH: 1128
<212> TYPE: DNA
<213> ORGANISM: Artificial Sequence
<220> FEATURE:
<223> OTHER INFORMATION: Description of Artificial Sequence: coding
      sequence for OmpA-K2S fusion protein

```
<400> SEQUENCE: 5
atgaaaaaga cagctatcgc gattgcagtg gcactggctg gtttcgctac cgtggcccag      60
gcggcctctg agggaaacag tgactgctac tttgggaatg ggtcagccta ccgtggcacg     120
cacagcctca ccgagtcggg tgcctcctgc ctcccgtgga attccatgat cctgataggc     180
aaggtttaca cagcacagaa ccccagtgcc caggcactgg gcctgggcaa acataattac     240
tgccggaatc ctgatgggga tgccaagccc tggtgccacg tgctgaagaa ccgcaggctg     300
acgtgggagt actgtgatgt gccctcctgc tccacctgcg gcctgagaca gtacagccag     360
cctcagtttc gcatcaaagg agggctcttc gccgacatcg cctcccaccc ctggcaggct     420
gccatctttg ccaagcacag gaggtcgccc ggagagcggt tcctgtgcgg ggcatactc     480 atcagctcct gctggattct ctctgccgcc cactgcttcc aggagaggtt ccgcccac      540 cacctgacgg tgatcttggg cagaacatac cgggtggtcc ctggcgagga ggagcagaaa    600
tttgaagtcg aaaaatacat tgtccataag gaattcgatg atgacactta cgacaatgac     660
attgcgctgc tgcagctgaa atcggattcg tcccgctgtg cccaggagag cagcgtggtc     720
cgcactgtgt gccttccccc ggcggacctg cagctgccgg actggacgga gtgtgagctc     780
tccggctacg gcaagcatga ggccttgtct ccttttctatt cggagcggct gaaggaggct     840
catgtcagac tgtacccatc cagccgctgc acatcacaac atttacttaa cagaacagtc     900
```

| accgacaaca tgctgtgtgc tggagacact cggagcggcg ggccccaggc aaacttgcac | 960 |
| gacgcctgcc agggcgattc gggaggcccc ctggtgtgtc tgaacgatgg ccgcatgact | 1020 |
| ttggtgggca tcatcagctg gggcctgggc tgtggacaga aggatgtccc gggtgtgtac | 1080 |
| acaaaggtta ccaactacct agactggatt cgtgacaaca tgcgaccg | 1128 |

<210> SEQ ID NO 6
<211> LENGTH: 66
<212> TYPE: DNA
<213> ORGANISM: Escherichia coli

<400> SEQUENCE: 6

| atgaaaaaga cagctatcgc gattgcagtg gcactggctg gtttcgctac cgtggcccag | 60 |
| gcggcc | 66 |

<210> SEQ ID NO 7
<211> LENGTH: 1065
<212> TYPE: DNA
<213> ORGANISM: Artificial Sequence
<220> FEATURE:
<223> OTHER INFORMATION: Description of Artificial Sequence: coding
   sequence for K2S protein

<400> SEQUENCE: 7

| tctgagggaa acagtgactg ctactttggg aatgggtcag cctaccgtgg cacgcacagc | 60 |
| ctcaccgagt cgggtgcctc ctgcctcccg tggaattcca tgatcctgat aggcaaggtt | 120 |
| tacacagcac agaaccccag tgcccaggca ctgggcctgg gcaaacataa ttactgccgg | 180 |
| aatcctgatg gggatgccaa gccctggtgc cacgtgctga agaaccgcag gctgacgtgg | 240 |
| gagtactgtg atgtgccctc ctgctccacc tgcggcctga cagtacag ccagcctcag | 300 |
| tttcgcatca aggagggct cttcgccgac atcgcctccc accctggca ggctgccatc | 360 |
| tttgccaagc acaggaggtc gccccggagag cggttcctgt gcgggggcat actcatcagc | 420 |
| tcctgctgga ttctctctgc cgcccactgc ttccaggaga ggtttccgcc ccaccacctg | 480 |
| acggtgatct tgggcagaac ataccgggtg gtccctggcg aggaggagca gaaatttgaa | 540 |
| gtcgaaaaat acattgtcca taaggaattc gatgatgaca cttacgacaa tgacattgcg | 600 |
| ctgctgcagc tgaaatcgga ttcgtcccgc tgtgcccagg agagcagcgt ggtccgcact | 660 |
| gtgtgccttc ccccggcgga cctgcagctg ccggactgga cggagtgtga gctctccggc | 720 |
| tacggcaagc atgaggcctt gtctcctttc tattcggagc ggctgaagga ggctcatgtc | 780 |
| agactgtacc catccagccg ctgcacatca aacatttac ttaacagaac agtcaccgac | 840 |
| aacatgctgt gtgctggaga cactcggagc ggcgggcccc aggcaaactt gcacgacgcc | 900 |
| tgccagggcg attcgggagg ccccctggtg tgtctgaacg atggccgcat gactttggtg | 960 |
| ggcatcatca gctggggcct gggctgtgga cagaaggatg tcccgggtgt gtacacaaag | 1020 |
| gttaccaact acctagactg gattcgtgac aacatgcgac cgtga | 1065 |

<210> SEQ ID NO 8
<211> LENGTH: 377
<212> TYPE: PRT
<213> ORGANISM: Artificial Sequence
<220> FEATURE:
<223> OTHER INFORMATION: Description of Artificial Sequence: OmpA-K2S
   fusion protein

<400> SEQUENCE: 8

Met Lys Lys Thr Ala Ile Ala Ile Ala Val Ala Leu Ala Gly Phe Ala

```
                  1               5              10              15
        Thr Val Ala Gln Ala Ala Ser Glu Gly Asn Ser Asp Cys Tyr Phe Gly
                         20              25              30
        Asn Gly Ser Ala Tyr Arg Gly Thr His Ser Leu Thr Glu Ser Gly Ala
                     35              40              45
        Ser Cys Leu Pro Trp Asn Ser Met Ile Leu Ile Gly Lys Val Tyr Thr
         50              55              60
        Ala Gln Asn Pro Ser Ala Gln Ala Leu Gly Leu Gly Lys His Asn Tyr
         65              70              75              80
        Cys Arg Asn Pro Asp Gly Asp Ala Lys Pro Trp Cys His Val Leu Lys
                         85              90              95
        Asn Arg Arg Leu Thr Trp Glu Tyr Cys Asp Val Pro Ser Cys Ser Thr
                        100             105             110
        Cys Gly Leu Arg Gln Tyr Ser Gln Pro Gln Phe Arg Ile Lys Gly Gly
                    115             120             125
        Leu Phe Ala Asp Ile Ala Ser His Pro Trp Gln Ala Ala Ile Phe Ala
        130             135             140
        Lys His Arg Arg Ser Pro Gly Glu Arg Phe Leu Cys Gly Gly Ile Leu
        145             150             155             160
        Ile Ser Ser Cys Trp Ile Leu Ser Ala Ala His Cys Phe Gln Glu Arg
                        165             170             175
        Phe Pro Pro His His Leu Thr Val Ile Leu Gly Arg Thr Tyr Arg Val
                    180             185             190
        Val Pro Gly Glu Glu Glu Gln Lys Phe Glu Val Glu Lys Tyr Ile Val
                    195             200             205
        His Lys Glu Phe Asp Asp Asp Thr Tyr Asp Asn Asp Ile Ala Leu Leu
                    210             215             220
        Gln Leu Lys Ser Asp Ser Ser Arg Cys Ala Gln Glu Ser Ser Val Val
        225             230             235             240
        Arg Thr Val Cys Leu Pro Pro Ala Asp Leu Gln Leu Pro Asp Trp Thr
                        245             250             255
        Glu Cys Glu Leu Ser Gly Tyr Gly Lys His Glu Ala Leu Ser Pro Phe
                    260             265             270
        Tyr Ser Glu Arg Leu Lys Glu Ala His Val Arg Leu Tyr Pro Ser Ser
                    275             280             285
        Arg Cys Thr Ser Gln His Leu Leu Asn Arg Thr Val Thr Asp Asn Met
                    290             295             300
        Leu Cys Ala Gly Asp Thr Arg Ser Gly Gly Pro Gln Ala Asn Leu His
        305             310             315             320
        Asp Ala Cys Gln Gly Asp Ser Gly Gly Pro Leu Val Cys Leu Asn Asp
                        325             330             335
        Gly Arg Met Thr Leu Val Gly Ile Ile Ser Trp Gly Leu Gly Cys Gly
                    340             345             350
        Gln Lys Asp Val Pro Gly Val Tyr Thr Lys Val Thr Asn Tyr Leu Asp
                    355             360             365
        Trp Ile Arg Asp Asn Met Arg Pro Gly
        370             375
```

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: peptide
      sequence

```
<400> SEQUENCE: 9

Ser Glu Gly Asn
  1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: peptide
      sequence

<400> SEQUENCE: 10

Ser Glu Gly Asn Ser Asp
  1               5

<210> SEQ ID NO 11
<211> LENGTH: 354
<212> TYPE: PRT
<213> ORGANISM: Artificial Sequence
<220> FEATURE:
<223> OTHER INFORMATION: Description of Artificial Sequence: K2S 174-527

<400> SEQUENCE: 11

Ser Glu Gly Asn Ser Asp Cys Tyr Phe Gly Asn Gly Ser Ala Tyr Arg
  1               5                  10                  15

Gly Thr His Ser Leu Thr Glu Ser Gly Ala Ser Cys Leu Pro Trp Asn
             20                  25                  30

Ser Met Ile Leu Ile Gly Lys Val Tyr Thr Ala Gln Asn Pro Ser Ala
         35                  40                  45

Gln Ala Leu Gly Leu Gly Lys His Asn Tyr Cys Arg Asn Pro Asp Gly
     50                  55                  60

Asp Ala Lys Pro Trp Cys His Val Leu Lys Asn Arg Arg Leu Thr Trp
 65                  70                  75                  80

Glu Tyr Cys Asp Val Pro Ser Cys Ser Thr Cys Gly Leu Arg Gln Tyr
                 85                  90                  95

Ser Gln Pro Gln Phe Arg Ile Lys Gly Gly Leu Phe Ala Asp Ile Ala
            100                 105                 110

Ser His Pro Trp Gln Ala Ala Ile Phe Ala Lys His Arg Arg Ser Pro
        115                 120                 125

Gly Glu Arg Phe Leu Cys Gly Gly Ile Leu Ile Ser Ser Cys Trp Ile
    130                 135                 140

Leu Ser Ala Ala His Cys Phe Gln Glu Arg Phe Pro Pro His His Leu
145                 150                 155                 160

Thr Val Ile Leu Gly Arg Thr Tyr Arg Val Val Pro Gly Glu Glu Glu
                165                 170                 175

Gln Lys Phe Glu Val Glu Lys Tyr Ile Val His Lys Glu Phe Asp Asp
            180                 185                 190

Asp Thr Tyr Asp Asn Asp Ile Ala Leu Leu Gln Leu Lys Ser Asp Ser
        195                 200                 205

Ser Arg Cys Ala Gln Glu Ser Ser Val Val Arg Thr Val Cys Leu Pro
    210                 215                 220

Pro Ala Asp Leu Gln Leu Pro Asp Trp Thr Glu Cys Glu Leu Ser Gly
225                 230                 235                 240

Tyr Gly Lys His Glu Ala Leu Ser Pro Phe Tyr Ser Glu Arg Leu Lys
                245                 250                 255

Glu Ala His Val Arg Leu Tyr Pro Ser Ser Arg Cys Thr Ser Gln His
```

-continued

```
            260                 265                 270
Leu Leu Asn Arg Thr Val Thr Asp Asn Met Leu Cys Ala Gly Asp Thr
            275                 280                 285

Arg Ser Gly Gly Pro Gln Ala Asn Leu His Asp Ala Cys Gln Gly Asp
        290                 295                 300

Ser Gly Gly Pro Leu Val Cys Leu Asn Asp Gly Arg Met Thr Leu Val
305                 310                 315                 320

Gly Ile Ile Ser Trp Gly Leu Gly Cys Gly Gln Lys Asp Val Pro Gly
                325                 330                 335

Val Tyr Thr Lys Val Thr Asn Tyr Leu Asp Trp Ile Arg Asp Asn Met
            340                 345                 350

Arg Pro

<210> SEQ ID NO 12
<211> LENGTH: 331
<212> TYPE: PRT
<213> ORGANISM: Artificial Sequence
<220> FEATURE:
<223> OTHER INFORMATION: Description of Artificial Sequence: K2S 197-527

<400> SEQUENCE: 12

Ser Gly Ala Ser Cys Leu Pro Trp Asn Ser Met Ile Leu Ile Gly Lys
  1               5                  10                  15

Val Tyr Thr Ala Gln Asn Pro Ser Ala Gln Ala Leu Gly Leu Gly Lys
             20                  25                  30

His Asn Tyr Cys Arg Asn Pro Asp Gly Asp Ala Lys Pro Trp Cys His
         35                  40                  45

Val Leu Lys Asn Arg Arg Leu Thr Trp Glu Tyr Cys Asp Val Pro Ser
     50                  55                  60

Cys Ser Thr Cys Gly Leu Arg Gln Tyr Ser Gln Pro Gln Phe Arg Ile
 65                  70                  75                  80

Lys Gly Gly Leu Phe Ala Asp Ile Ala Ser His Pro Trp Gln Ala Ala
                 85                  90                  95

Ile Phe Ala Lys His Arg Arg Ser Pro Gly Glu Arg Phe Leu Cys Gly
            100                 105                 110

Gly Ile Leu Ile Ser Ser Cys Trp Ile Leu Ser Ala Ala His Cys Phe
        115                 120                 125

Gln Glu Arg Phe Pro Pro His His Leu Thr Val Ile Leu Gly Arg Thr
    130                 135                 140

Tyr Arg Val Val Pro Gly Glu Glu Glu Gln Lys Phe Glu Val Glu Lys
145                 150                 155                 160

Tyr Ile Val His Lys Glu Phe Asp Asp Asp Thr Tyr Asp Asn Asp Ile
                165                 170                 175

Ala Leu Leu Gln Leu Lys Ser Asp Ser Ser Arg Cys Ala Gln Glu Ser
            180                 185                 190

Ser Val Val Arg Thr Val Cys Leu Pro Pro Ala Asp Leu Gln Leu Pro
        195                 200                 205

Asp Trp Thr Glu Cys Glu Leu Ser Gly Tyr Gly Lys His Glu Ala Leu
    210                 215                 220

Ser Pro Phe Tyr Ser Glu Arg Leu Lys Glu Ala His Val Arg Leu Tyr
225                 230                 235                 240

Pro Ser Ser Arg Cys Thr Ser Gln His Leu Leu Asn Arg Thr Val Thr
                245                 250                 255

Asp Asn Met Leu Cys Ala Gly Asp Thr Arg Ser Gly Gly Pro Gln Ala
            260                 265                 270
```

```
Asn Leu His Asp Ala Cys Gln Gly Asp Ser Gly Gly Pro Leu Val Cys
        275                 280                 285

Leu Asn Asp Gly Arg Met Thr Leu Val Gly Ile Ile Ser Trp Gly Leu
        290                 295                 300

Gly Cys Gly Gln Lys Asp Val Pro Gly Val Tyr Thr Lys Val Thr Asn
305                 310                 315                 320

Tyr Leu Asp Trp Ile Arg Asp Asn Met Arg Pro
                325                 330

<210> SEQ ID NO 13
<211> LENGTH: 339
<212> TYPE: PRT
<213> ORGANISM: Artificial Sequence
<220> FEATURE:
<223> OTHER INFORMATION: Description of Artificial Sequence: K2S
      193-527, modified

<400> SEQUENCE: 13

Ser Glu Gly Asn Ser Leu Thr Glu Ser Gly Ala Ser Cys Leu Pro Trp
  1               5                  10                  15

Asn Ser Met Ile Leu Ile Gly Lys Val Tyr Thr Ala Gln Asn Pro Ser
             20                  25                  30

Ala Gln Ala Leu Gly Leu Gly Lys His Asn Tyr Cys Arg Asn Pro Asp
         35                  40                  45

Gly Asp Ala Lys Pro Trp Cys His Val Leu Lys Asn Arg Arg Leu Thr
     50                  55                  60

Trp Glu Tyr Cys Asp Val Pro Ser Cys Ser Thr Cys Gly Leu Arg Gln
 65                  70                  75                  80

Tyr Ser Gln Pro Gln Phe Arg Ile Lys Gly Gly Leu Phe Ala Asp Ile
                 85                  90                  95

Ala Ser His Pro Trp Gln Ala Ala Ile Phe Ala Lys His Arg Arg Ser
            100                 105                 110

Pro Gly Glu Arg Phe Leu Cys Gly Gly Ile Leu Ile Ser Ser Cys Trp
        115                 120                 125

Ile Leu Ser Ala Ala His Cys Phe Gln Glu Arg Phe Pro Pro His His
130                 135                 140

Leu Thr Val Ile Leu Gly Arg Thr Tyr Arg Val Val Pro Gly Glu Glu
145                 150                 155                 160

Glu Gln Lys Phe Glu Val Glu Lys Tyr Ile Val His Lys Glu Phe Asp
                165                 170                 175

Asp Asp Thr Tyr Asp Asn Asp Ile Ala Leu Leu Gln Leu Lys Ser Asp
            180                 185                 190

Ser Ser Arg Cys Ala Gln Glu Ser Ser Val Val Arg Thr Val Cys Leu
        195                 200                 205

Pro Pro Ala Asp Leu Gln Leu Pro Asp Trp Thr Glu Cys Glu Leu Ser
210                 215                 220

Gly Tyr Gly Lys His Glu Ala Leu Ser Pro Phe Tyr Ser Glu Arg Leu
225                 230                 235                 240

Lys Glu Ala His Val Arg Leu Tyr Pro Ser Ser Arg Cys Thr Ser Gln
                245                 250                 255

His Leu Leu Asn Arg Thr Val Thr Asp Asn Met Leu Cys Ala Gly Asp
            260                 265                 270

Thr Arg Ser Gly Gly Pro Gln Ala Asn Leu His Asp Ala Cys Gln Gly
        275                 280                 285

Asp Ser Gly Gly Pro Leu Val Cys Leu Asn Asp Gly Arg Met Thr Leu
```

-continued

```
            290                 295                 300
Val Gly Ile Ile Ser Trp Gly Leu Gly Cys Gly Gln Lys Asp Val Pro
305                 310                 315                 320

Gly Val Tyr Thr Lys Val Thr Asn Tyr Leu Asp Trp Ile Arg Asp Asn
                325                 330                 335

Met Arg Pro

<210> SEQ ID NO 14
<211> LENGTH: 335
<212> TYPE: PRT
<213> ORGANISM: Artificial Sequence
<220> FEATURE:
<223> OTHER INFORMATION: Description of Artificial Sequence: K2S
      193-527, modified

<400> SEQUENCE: 14

Ser Leu Thr Glu Ser Gly Ala Ser Cys Leu Pro Trp Asn Ser Met Ile
  1               5                  10                  15

Leu Ile Gly Lys Val Tyr Thr Ala Gln Asn Pro Ser Ala Gln Ala Leu
                 20                  25                  30

Gly Leu Gly Lys His Asn Tyr Cys Arg Asn Pro Asp Gly Asp Ala Lys
             35                  40                  45

Pro Trp Cys His Val Leu Lys Asn Arg Arg Leu Thr Trp Glu Tyr Cys
 50                  55                  60

Asp Val Pro Ser Ser Thr Cys Gly Leu Arg Gln Tyr Ser Gln Pro
 65                  70                  75                  80

Gln Phe Arg Ile Lys Gly Gly Leu Phe Ala Asp Ile Ala Ser His Pro
                 85                  90                  95

Trp Gln Ala Ala Ile Phe Ala Lys His Arg Arg Ser Pro Gly Glu Arg
            100                 105                 110

Phe Leu Cys Gly Gly Ile Leu Ile Ser Ser Cys Trp Ile Leu Ser Ala
            115                 120                 125

Ala His Cys Phe Gln Glu Arg Phe Pro Pro His His Leu Thr Val Ile
130                 135                 140

Leu Gly Arg Thr Tyr Arg Val Val Pro Gly Glu Glu Gln Lys Phe
145                 150                 155                 160

Glu Val Glu Lys Tyr Ile Val His Lys Glu Phe Asp Asp Thr Tyr
                165                 170                 175

Asp Asn Asp Ile Ala Leu Leu Gln Leu Lys Ser Asp Ser Ser Arg Cys
            180                 185                 190

Ala Gln Glu Ser Ser Val Val Arg Thr Val Cys Leu Pro Pro Ala Asp
            195                 200                 205

Leu Gln Leu Pro Asp Trp Thr Glu Cys Glu Leu Ser Gly Tyr Gly Lys
            210                 215                 220

His Glu Ala Leu Ser Pro Phe Tyr Ser Glu Arg Leu Lys Glu Ala His
225                 230                 235                 240

Val Arg Leu Tyr Pro Ser Ser Arg Cys Thr Ser Gln His Leu Leu Asn
                245                 250                 255

Arg Thr Val Thr Asp Asn Met Leu Cys Ala Gly Asp Thr Arg Ser Gly
            260                 265                 270

Gly Pro Gln Ala Asn Leu His Asp Ala Cys Gln Gly Asp Ser Gly Gly
        275                 280                 285

Pro Leu Val Cys Leu Asn Asp Gly Arg Met Thr Leu Val Gly Ile Ile
        290                 295                 300

Ser Trp Gly Leu Gly Cys Gly Gln Lys Asp Val Pro Gly Val Tyr Thr
```

```
                305                 310                 315                 320
Lys Val Thr Asn Tyr Leu Asp Trp Ile Arg Asp Asn Met Arg Pro
                    325                 330                 335

<210> SEQ ID NO 15
<211> LENGTH: 343
<212> TYPE: PRT
<213> ORGANISM: Artificial Sequence
<220> FEATURE:
<223> OTHER INFORMATION: Description of Artificial Sequence: K2S
      191-527, modified

<400> SEQUENCE: 15

Ser Glu Gly Asn Ser Asp Thr His Ser Leu Thr Glu Ser Gly Ala Ser
  1               5                  10                  15

Cys Leu Pro Trp Asn Ser Met Ile Leu Ile Gly Lys Val Tyr Thr Ala
                 20                  25                  30

Gln Asn Pro Ser Ala Gln Ala Leu Gly Leu Gly Lys His Asn Tyr Cys
             35                  40                  45

Arg Asn Pro Asp Gly Asp Ala Lys Pro Trp Cys His Val Leu Lys Asn
 50                  55                  60

Arg Arg Leu Thr Trp Glu Tyr Cys Asp Val Pro Ser Cys Ser Thr Cys
 65                  70                  75                  80

Gly Leu Arg Gln Tyr Ser Gln Pro Gln Phe Arg Ile Lys Gly Gly Leu
                 85                  90                  95

Phe Ala Asp Ile Ala Ser His Pro Trp Gln Ala Ala Ile Phe Ala Lys
                100                 105                 110

His Arg Arg Ser Pro Gly Glu Arg Phe Leu Cys Gly Gly Ile Leu Ile
            115                 120                 125

Ser Ser Cys Trp Ile Leu Ser Ala Ala His Cys Phe Gln Glu Arg Phe
130                 135                 140

Pro Pro His His Leu Thr Val Ile Leu Gly Arg Thr Tyr Arg Val Val
145                 150                 155                 160

Pro Gly Glu Glu Glu Gln Lys Phe Glu Val Glu Lys Tyr Ile Val His
                165                 170                 175

Lys Glu Phe Asp Asp Asp Thr Tyr Asp Asn Asp Ile Ala Leu Leu Gln
            180                 185                 190

Leu Lys Ser Asp Ser Ser Arg Cys Ala Gln Glu Ser Ser Val Val Arg
            195                 200                 205

Thr Val Cys Leu Pro Pro Ala Asp Leu Gln Leu Pro Asp Trp Thr Glu
210                 215                 220

Cys Glu Leu Ser Gly Tyr Gly Lys His Glu Ala Leu Ser Pro Phe Tyr
225                 230                 235                 240

Ser Glu Arg Leu Lys Glu Ala His Val Arg Leu Tyr Pro Ser Ser Arg
                245                 250                 255

Cys Thr Ser Gln His Leu Leu Asn Arg Thr Val Thr Asp Asn Met Leu
            260                 265                 270

Cys Ala Gly Asp Thr Arg Ser Gly Gly Pro Gln Ala Asn Leu His Asp
            275                 280                 285

Ala Cys Gln Gly Asp Ser Gly Gly Pro Leu Val Cys Leu Asn Asp Gly
            290                 295                 300

Arg Met Thr Leu Val Gly Ile Ile Ser Trp Gly Leu Gly Cys Gly Gln
305                 310                 315                 320

Lys Asp Val Pro Gly Val Tyr Thr Lys Val Thr Asn Tyr Leu Asp Trp
                325                 330                 335
```

Ile Arg Asp Asn Met Arg Pro
              340

<210> SEQ ID NO 16
<211> LENGTH: 343
<212> TYPE: PRT
<213> ORGANISM: Artificial Sequence
<220> FEATURE:
<223> OTHER INFORMATION: Description of Artificial Sequence: K2S
      191-527, modified

<400> SEQUENCE: 16

Ser Glu Gly Asn Ser Asp Thr His Ser Leu Thr Glu Ser Gly Ala Ser
 1               5                  10                  15

Cys Leu Pro Trp Asn Ser Met Ile Leu Ile Gly Lys Val Tyr Thr Ala
                20                  25                  30

Gln Asn Pro Ser Ala Gln Ala Leu Gly Leu Gly Lys His Asn Tyr Cys
            35                  40                  45

Arg Asn Pro Asp Gly Asp Ala Lys Pro Trp Cys His Val Leu Lys Asn
 50                  55                  60

Arg Arg Leu Thr Trp Glu Tyr Cys Asp Val Pro Ser Ser Ser Thr Cys
 65                  70                  75                  80

Gly Leu Arg Gln Tyr Ser Gln Pro Gln Phe Arg Ile Lys Gly Gly Leu
                85                  90                  95

Phe Ala Asp Ile Ala Ser His Pro Trp Gln Ala Ala Ile Phe Ala Lys
                100                 105                 110

His Arg Arg Ser Pro Gly Glu Arg Phe Leu Cys Gly Gly Ile Leu Ile
            115                 120                 125

Ser Ser Cys Trp Ile Leu Ser Ala Ala His Cys Phe Gln Glu Arg Phe
130                 135                 140

Pro Pro His His Leu Thr Val Ile Leu Gly Arg Thr Tyr Arg Val Val
145                 150                 155                 160

Pro Gly Glu Glu Glu Gln Lys Phe Glu Val Glu Lys Tyr Ile Val His
                165                 170                 175

Lys Glu Phe Asp Asp Asp Thr Tyr Asp Asn Asp Ile Ala Leu Leu Gln
                180                 185                 190

Leu Lys Ser Asp Ser Ser Arg Cys Ala Gln Glu Ser Ser Val Val Arg
            195                 200                 205

Thr Val Cys Leu Pro Pro Ala Asp Leu Gln Leu Pro Asp Trp Thr Glu
210                 215                 220

Cys Glu Leu Ser Gly Tyr Gly Lys His Glu Ala Leu Ser Pro Phe Tyr
225                 230                 235                 240

Ser Glu Arg Leu Lys Glu Ala His Val Arg Leu Tyr Pro Ser Ser Arg
                245                 250                 255

Cys Thr Ser Gln His Leu Leu Asn Arg Thr Val Thr Asp Asn Met Leu
            260                 265                 270

Cys Ala Gly Asp Thr Arg Ser Gly Gly Pro Gln Ala Asn Leu His Asp
        275                 280                 285

Ala Cys Gln Gly Asp Ser Gly Gly Pro Leu Val Cys Leu Asn Asp Gly
290                 295                 300

Arg Met Thr Leu Val Gly Ile Ile Ser Trp Gly Leu Gly Cys Gly Gln
305                 310                 315                 320

Lys Asp Val Pro Gly Val Tyr Thr Lys Val Thr Asn Tyr Leu Asp Trp
                325                 330                 335

Ile Arg Asp Asn Met Arg Pro
              340

<210> SEQ ID NO 17
<211> LENGTH: 308
<212> TYPE: PRT
<213> ORGANISM: Artificial Sequence
<220> FEATURE:
<223> OTHER INFORMATION: Description of Artificial Sequence: K2S 220-527

<400> SEQUENCE: 17

```
Ser Ala Gln Ala Leu Gly Leu Gly Lys His Asn Tyr Cys Arg Asn Pro
  1               5                  10                  15

Asp Gly Asp Ala Lys Pro Trp Cys His Val Leu Lys Asn Arg Arg Leu
             20                  25                  30

Thr Trp Glu Tyr Cys Asp Val Pro Ser Cys Ser Thr Cys Gly Leu Arg
         35                  40                  45

Gln Tyr Ser Gln Pro Gln Phe Arg Ile Lys Gly Gly Leu Phe Ala Asp
     50                  55                  60

Ile Ala Ser His Pro Trp Gln Ala Ala Ile Phe Ala Lys His Arg Arg
 65                  70                  75                  80

Ser Pro Gly Glu Arg Phe Leu Cys Gly Gly Ile Leu Ile Ser Ser Cys
                 85                  90                  95

Trp Ile Leu Ser Ala Ala His Cys Phe Gln Glu Arg Phe Pro Pro His
            100                 105                 110

His Leu Thr Val Ile Leu Gly Arg Thr Tyr Arg Val Val Pro Gly Glu
        115                 120                 125

Glu Glu Gln Lys Phe Glu Val Glu Lys Tyr Ile Val His Lys Glu Phe
    130                 135                 140

Asp Asp Asp Thr Tyr Asp Asn Asp Ile Ala Leu Leu Gln Leu Lys Ser
145                 150                 155                 160

Asp Ser Ser Arg Cys Ala Gln Glu Ser Ser Val Val Arg Thr Val Cys
                165                 170                 175

Leu Pro Pro Ala Asp Leu Gln Leu Pro Asp Trp Thr Glu Cys Glu Leu
            180                 185                 190

Ser Gly Tyr Gly Lys His Glu Ala Leu Ser Pro Phe Tyr Ser Glu Arg
        195                 200                 205

Leu Lys Glu Ala His Val Arg Leu Tyr Pro Ser Ser Arg Cys Thr Ser
    210                 215                 220

Gln His Leu Leu Asn Arg Thr Val Thr Asp Asn Met Leu Cys Ala Gly
225                 230                 235                 240

Asp Thr Arg Ser Gly Gly Pro Gln Ala Asn Leu His Asp Ala Cys Gln
                245                 250                 255

Gly Asp Ser Gly Gly Pro Leu Val Cys Leu Asn Asp Gly Arg Met Thr
            260                 265                 270

Leu Val Gly Ile Ile Ser Trp Gly Leu Gly Cys Gly Gln Lys Asp Val
        275                 280                 285

Pro Gly Val Tyr Thr Lys Val Thr Asn Tyr Leu Asp Trp Ile Arg Asp
    290                 295                 300

Asn Met Arg Pro
305
```

<210> SEQ ID NO 18
<211> LENGTH: 268
<212> TYPE: PRT
<213> ORGANISM: Artificial Sequence
<220> FEATURE:
<223> OTHER INFORMATION: Description of Artificial Sequence: K2S 260-527

```
<400> SEQUENCE: 18

Ser Cys Ser Thr Cys Gly Leu Arg Gln Tyr Ser Gln Pro Gln Phe Arg
 1               5                  10                  15

Ile Lys Gly Gly Leu Phe Ala Asp Ile Ala Ser His Pro Trp Gln Ala
            20                  25                  30

Ala Ile Phe Ala Lys His Arg Arg Ser Pro Gly Glu Arg Phe Leu Cys
        35                  40                  45

Gly Gly Ile Leu Ile Ser Ser Cys Trp Ile Leu Ser Ala Ala His Cys
    50                  55                  60

Phe Gln Glu Arg Phe Pro Pro His His Leu Thr Val Ile Leu Gly Arg
65                  70                  75                  80

Thr Tyr Arg Val Val Pro Gly Glu Glu Gln Lys Phe Glu Val
                85                  90                  95

Lys Tyr Ile Val His Lys Glu Phe Asp Asp Asp Thr Tyr Asp Asn Asp
                100                 105                 110

Ile Ala Leu Leu Gln Leu Lys Ser Asp Ser Ser Arg Cys Ala Gln Glu
                115                 120                 125

Ser Ser Val Val Arg Thr Val Cys Leu Pro Pro Ala Asp Leu Gln Leu
    130                 135                 140

Pro Asp Trp Thr Glu Cys Glu Leu Ser Gly Tyr Gly Lys His Glu Ala
145                 150                 155                 160

Leu Ser Pro Phe Tyr Ser Glu Arg Leu Lys Glu Ala His Val Arg Leu
                165                 170                 175

Tyr Pro Ser Ser Arg Cys Thr Ser Gln His Leu Leu Asn Arg Thr Val
            180                 185                 190

Thr Asp Asn Met Leu Cys Ala Gly Asp Thr Arg Ser Gly Gly Pro Gln
        195                 200                 205

Ala Asn Leu His Asp Ala Cys Gln Gly Asp Ser Gly Gly Pro Leu Val
    210                 215                 220

Cys Leu Asn Asp Gly Arg Met Thr Leu Val Gly Ile Ile Ser Trp Gly
225                 230                 235                 240

Leu Gly Cys Gly Gln Lys Asp Val Pro Gly Val Tyr Thr Lys Val Thr
                245                 250                 255

Asn Tyr Leu Asp Trp Ile Arg Asp Asn Met Arg Pro
            260                 265

<210> SEQ ID NO 19
<211> LENGTH: 527
<212> TYPE: PRT
<213> ORGANISM: Homo sapiens

<400> SEQUENCE: 19

Ser Tyr Gln Val Ile Cys Arg Asp Glu Lys Thr Gln Met Ile Tyr Gln
 1               5                  10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95
```

```
Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
            115                 120                 125

Arg Arg Pro Asp Ala Ile Arg Leu Gly Leu Gly Asn His Asn Tyr Cys
            130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
            165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
            195                 200                 205

Leu Ile Gly Lys Val Tyr Thr Ala Gln Asn Pro Ser Ala Gln Ala Leu
            210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
            245                 250                 255

Asp Val Pro Ser Cys Ser Thr Cys Gly Leu Arg Gln Tyr Ser Gln Pro
            260                 265                 270

Gln Phe Arg Ile Lys Gly Gly Leu Phe Ala Asp Ile Ala Ser His Pro
            275                 280                 285

Trp Gln Ala Ala Ile Phe Ala Lys His Arg Arg Ser Pro Gly Glu Arg
            290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
            325                 330                 335

Leu Gly Arg Thr Tyr Arg Val Val Pro Gly Glu Glu Gln Lys Phe
            340                 345                 350

Glu Val Glu Lys Tyr Ile Val His Lys Glu Phe Asp Asp Thr Tyr
            355                 360                 365

Asp Asn Asp Ile Ala Leu Leu Gln Leu Lys Ser Asp Ser Ser Arg Cys
            370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
            450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
            485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
```

```
<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: coding
      sequence for SEGN

<400> SEQUENCE: 20
tctgagggaa ac                                                              12

<210> SEQ ID NO 21
<211> LENGTH: 22
<212> TYPE: PRT
<213> ORGANISM: Escherichia coli

<400> SEQUENCE: 21

Met Lys Lys Thr Ala Ile Ala Ile Ala Val Ala Leu Ala Gly Phe Ala
  1               5                  10                  15

Thr Val Ala Gln Ala Ala
            20

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 22
gaggaggagg tggcccaggc ggcctctgag ggaaacagtg ac                              42

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 23
gaggaggagc tggccggcct ggcccggtcg catgttgtca cg                              42

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 24
acatgcgacc gtgacaggcc ggccag                                               26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 25
ctggccggcc tgtcacggtc gcatgt                                               26

<210> SEQ ID NO 26
```

```
-continued

<211> LENGTH: 44
<212> TYPE: DNA
<213> ORGANISM: Artificial Sequence
<220> FEATURE:
<223> OTHER INFORMATION: Description of Artificial Sequence: K2S-gpIII
      junction

<400> SEQUENCE: 26
ttcgtgacaa catgcgaccg ggccaggccg gccaggaggg tggt              44
```

METHOD FOR LARGE SCALE PRODUCTION OF RECOMBINANT DNA-DERIVED TPA OR K2S MOLECULES

CROSS-REFERENCE TO RELATED APPLICATIONS

This application claims priority to U.S. Provisional Patent Application No. 60/268,574, filed Feb. 15, 2001, and to Great Britain Patent Application No. GB 00 27 779.8, filed Nov. 14, 2000. The full disclosure of each of these applications is herein incorporated by reference.

BACKGROUND OF THE INVENTION

1. Field of the Invention

The invention belongs to the field of thrombolysis and of tissue plasminogen activator (tPA) derivative production in prokaryotic cells.

The invention relates to methods for the production of a recombinant DNA-derived tPA, a variant therof or a (Kringle 2 Serine) K2S molecule or a variant therof in prokaryotic cells, wherein said tPA or K2S or variant is secreted extracellularly as an active and correctly folded protein, and the prokaryotic cell contains and expresses a vector comprising the DNA coding for said tPA or K2S or variant operably linked to the DNA coding for the signal peptide OmpA. The invention further relates to specific K2S derivatives obtainable by said method. The invention further relates to said DNA molecules and the use of said DNA molecules in said methods.

2. Related Art

Tissue plasminogen activator (tPA) is a polypeptide containing 527 amino acid residues (Pennica, D., et al., *Nature* 301:214–221 (1983)) with a molecular mass of 72 kDa. The molecule is divided into five structural domains. Nearby the N-terminal region is a looped finger domain, which is followed by a growth factor domain. Two similar domains, kringle 1 and kringle 2, are following. Both finger and kringle 2 domains bind specifically to the fibrin clots thereby accelerating tPA protein activation of bound plasminogen. Downstream of kringle 2 is the serine protease, with its catalytic site located at the C-terminus. The serine protease is responsible for converting plasminogen to plasmin a reaction important in the homeostasis of fibrin formation and clot dissolution. The correct folding of tPA requires the correct pairing of 17 disulfide bridges in the molecule (Allen, S., et al., *J. Biol. Chem.* 270:4797–4804 (1995)).

Clinically, tPA is a thrombolytic agent of choice for the treatment of acute myocardial infarction, pulmonary embolism, stroke, peripheral arterial occlusions, and other thromboembolic diseases. It has the advantage of causing no side effects on systemic haemorrhaging and fibrinogen depletion (Camiolo, S. M., et al., *Proc. Soc. Exp. Biol. Med.* 38:277–280 (1971)). Bowes melanoma cells were first used as a source in tPA production for therapeutic purposes (Griffiths, J. B. and Electricwala, A., *Adv. Biochem. Eng. Biotechnol.* 34:147–166 (1987)). Since a consistent process with efficient production of highly purified protein in good yield is required for clinical use, the construction of full-length recombinant-tPA (r-tPA) progressed to mammalian cells. Chinese hamster ovary cells were transfected with the tPA gene to synthesize the r-tPA (Cartwright, T., "Production of t-PA from animal cell culture," in *Animal Cell Biotechnology*, Vol 5, Spier and Griffiths eds., Academic Press, New York, N.Y. (1992), pp217–245; Lubiniecki, A., et al., "Selected strategies for manufacture and control of recombinant tissue plasminogen activator prepared from cell culture," in Spier, et al., eds., *Advances In Animal Cell Biology And Technology For Bioprocesses*, Butterworths, London, p. 442–451). The recombinant DNA derived product produced by a mammalian cell culture fermentation system is harvested and purified from the culture medium. Attracted by simplicity and economy of production, a number of efforts in producing r-tPA from microorganisms, expecially bacteria, and more especially from *Escherichia coli*, were investigated (Datar, R. V., et al., *Biotechnology* 11:349–357 (1993); Harris, T. J., et al., *Mol. Biol. Med.* 3:279–292 (1986); Sarmientos, P., et al., *Biotechnology* 7:495–501 (1989)). Regarding the low yield and the formation of inclusion bodies, which resulted in misfolding and in an inactive enzyme, numerous strategies have been proposed to overcome these problems.

Several deletion-mutant variants including kringle 2 plus serine protease (K2S) were considered. However, the enzymatic activity of the recombinant-K2S (r-K2S) was obtained only when refolding processes of purified inclusion bodies from cytoplasmic compartment were achieved (Hu, C. K., et al., *Biochemistry* 33:11760–11766 (1994); Saito, Y., et al., *Biotechnol. Prog.* 10:472–479 (1994)). In order to avoid the cumbersome refolding processes, impurities of misfolded proteins, and periplasmic protein delivery, special bacterial expression systems were exploited (Betton, J. M., et al., *J. Biol. Chem.* 273:8897–8902 (1998); Scherrer, S., et al., *Appl. Microbiol. Biotechnol.* 42:85–89 (1994)). Despite periplasmic expression of tPA, overexpression led to inactive aggregates, even in the relatively high oxidizing condition in the periplasm.

In the prior art, there are a few descriptions of methods for the preparation of recombinant K2S in *E. coli*. However, there is no disclosure of a method leading to a cost effective method for large scale production of biologically active K2S.

Obukowicz et al. (Obukowicz, M. G., et al., *Biochemistry* 29:9737–9745 (1990)) expressed and purified r-K2S from periplasmic space. The obvious disadvantage of this method was an extra periplasmic extraction step, which is not suitable for large scale production.

Saito et al. (Saito, Y., et al., *Biotechnol. Prog.* 10:472–479 (1994)) disclose the cytoplasmic expression of r-K2S. The authors used an in vivo renaturation processes for the expressed r-K2S, which was purified from the cytoplasmic space of *E. coli* as inclusion body. Boehringer Mannheim use a similar cumbersome denaturing/refolding process involving the steps of cell digestion, solubilization under denaturing and reducing conditions and reactivation under oxidizing conditions in the presence of GSH/GSSG which is not cost effective (Martin, U., et al., *Kardiol.* 79:167–170 (1990)) and requires mutation of the amino acid sequence with possibly antigenic potential.

In 1991, Waldenström et al. (Waldenström, M., et al., *Gene* 99:243–248 (1991)) constructed a vector (pEZZK2P) for the secretion of kringle 2 plus serine protease domain to *E. coli* culture supernatant. Hydroxylamine was used to remove the ZZ fusion peptide from IgG-Sepharose purified fraction. The cleavage agent hydroxylamine required modification of the cleavage sites of kringle 2 plus serine protease (Asn177→Ser and Asn184→Gln) thus to protect it from hydroxylamine digestion. However, the resulting non-native, not properly folded K2S molecule is not suitable for therapeutic purposes. No enzymatic activity regarding fibrin binding/protease activity was disclosed. The unusual sequence may even activate the human immune system.

SUMMARY OF THE INVENTION

The problem underlying the present invention was thus to provide a commercially applicable method for large scale production of tPA molecules and derivatives therof, e.g. K2S, wherein the K2S molecule is secreted in its biologically active form into the culture supernatant. The problem was solved within the scope of the claims and specification of the present invention.

BRIEF DESCRIPTION OF THE DRAWINGS/FIGURES

FIG. 1. Validation of PCR amplification product of the K2S gene from the p51-3 vector by using sK2/174 and ASSP primers. Lane 1 shows 1 kb marker (Roche Molecular Biochemicals, Indianapolis, Ind.). Lane 2 was loaded with 1 µl of amplified product. A single band at 1110 bp is depicted. The electrophoresis was performed on a 1% agarose gel.

Figure 2:
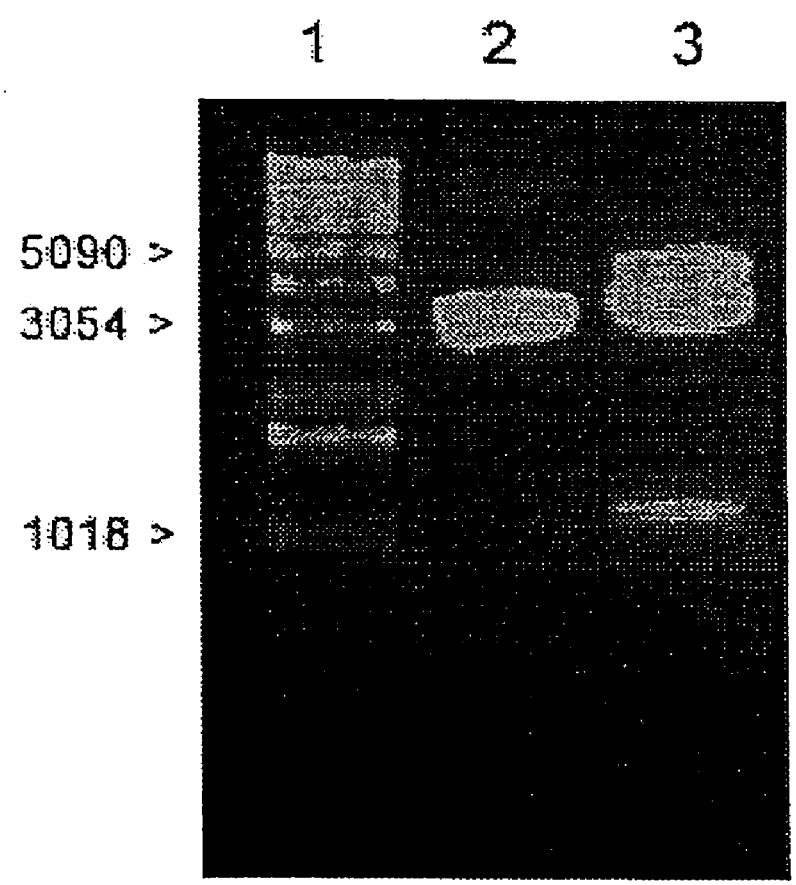

FIG. 2. Identification of inserted K2S gene at 1110 bp (*) after Sfi I digested pComb3H-K2S was demonstrated in lane 3. Lane 1 shows 1 kb marker. Lane 2 was loaded with uncut pComb3H-K2S. The electrophoresis was performed on a 1% agarose gel.

Figure 3:
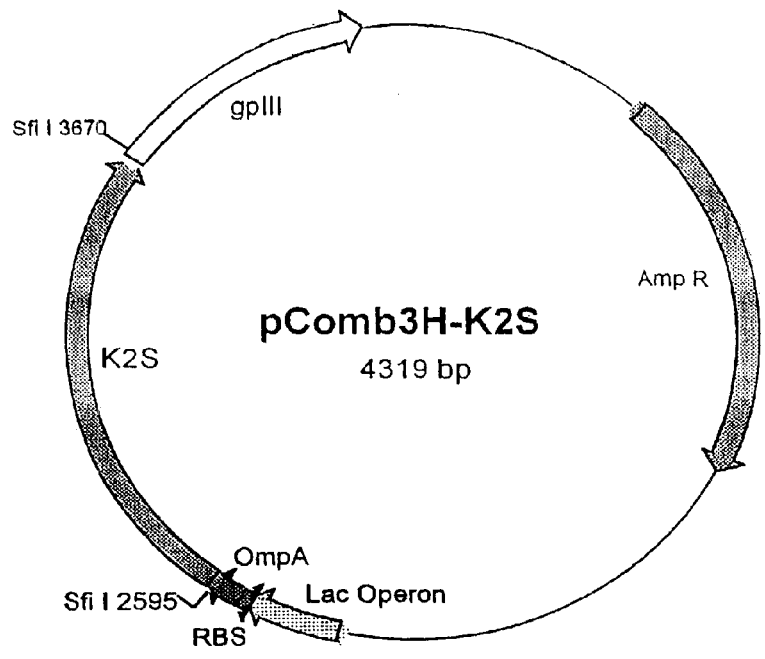

FIG. 3. Scheme of pComb3H-K2S showing two Sfi I cloning sites into which the K2S gene was inserted. Signal sequence (OmpA), ribosome binding site (RIBS), lac promotor, and gpIII gene are also depicted.

Figure 4:

FIG. 4. Schematic diagram of the mutation site at the junction between the K2S and gpIII genes on pComb3H-K2S. The annealing site of pComb3H-K2S is bound with a set of mutation primers (msTPA and masTPA) containing modified oligonucleosides (underlined). After performing the cycle amplification, the Sfi I site 1 (in bold) is modified and lost in the newly synthesized strand.

Figure 5:
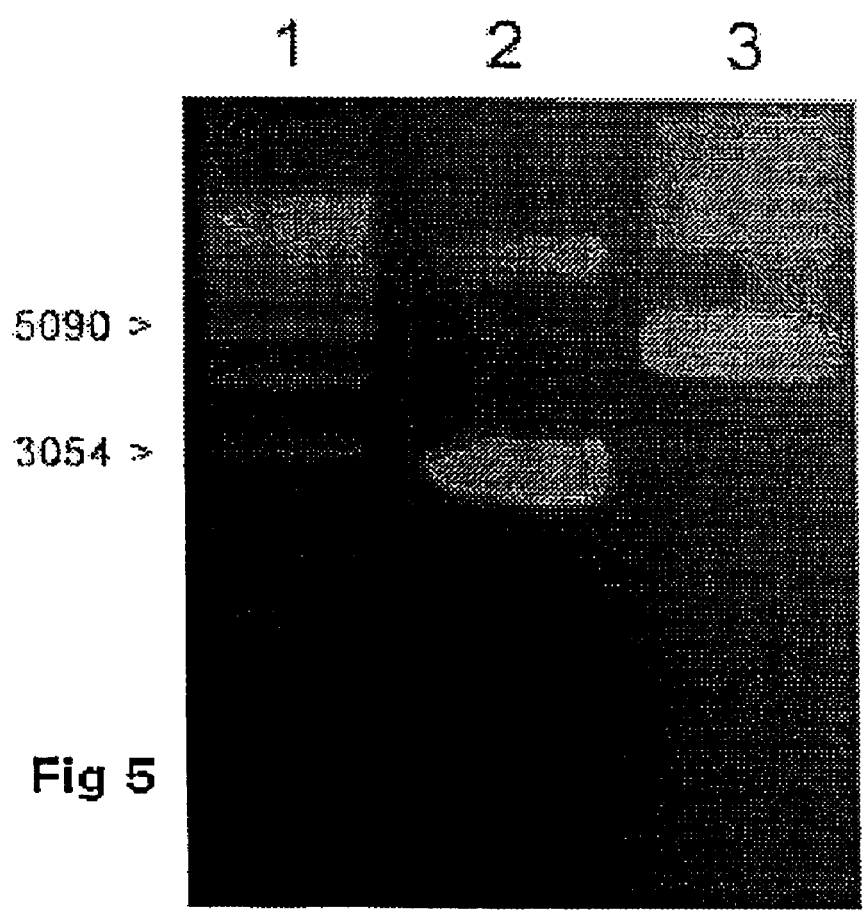

FIG. 5. Characterization of newly synthesized MpComb3H-K2S by the Sfi I restriction enzyme. A single band at 4319 bp that refers to a single cleavage site of MpComb3H-K2S is observed in lane 3. No inserted K2S band at 1110 bp can be visualized. Lane 1 shows 1 kb marker. Lane 2 was loaded with uncut MpComb3H-K2S. The electrophoresis was performed on a 1% agarose gel.

Figure 6:
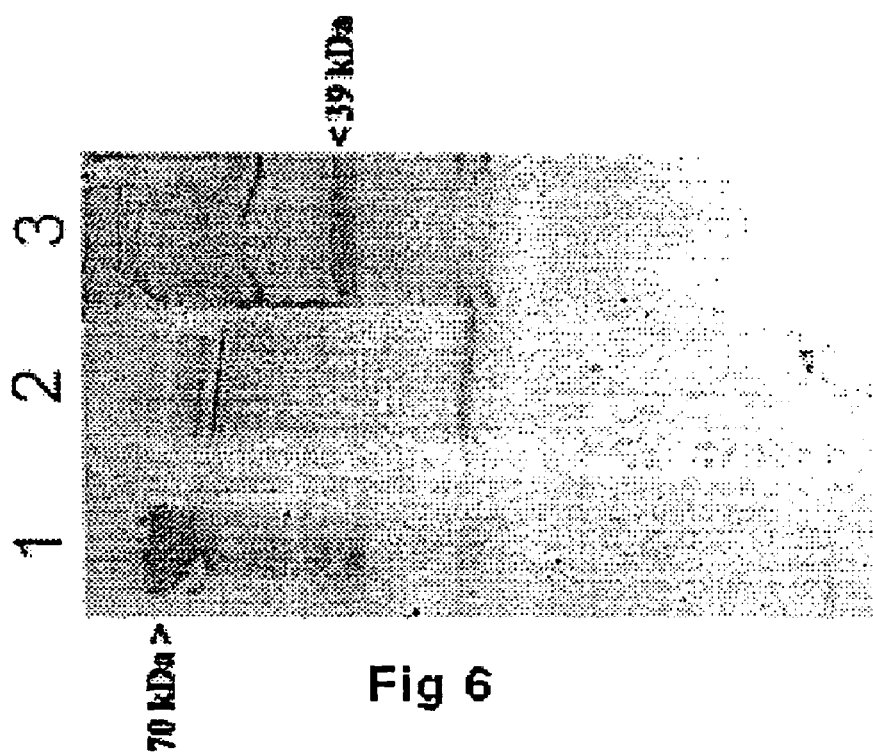

FIG. 6. Identification of immunological reactive band with of recombinant DNA-derived protein purified from XM[K2S] culture supernatant with sheep anti-tPA conjugated HRP. Lane 1 was loaded with 40 ng of standard melanoma tPA (86/670), which showed the reactive band at 70 kDa. The partially purified and concentrated culture supernatants from non-transformed E. coli XL1-Blue and XM[K2S] were applied to lane 2 and 3 respectively. The distinct reactive band was particularly demonstrated in lane 3 at 39 kDa.

Figure 7:
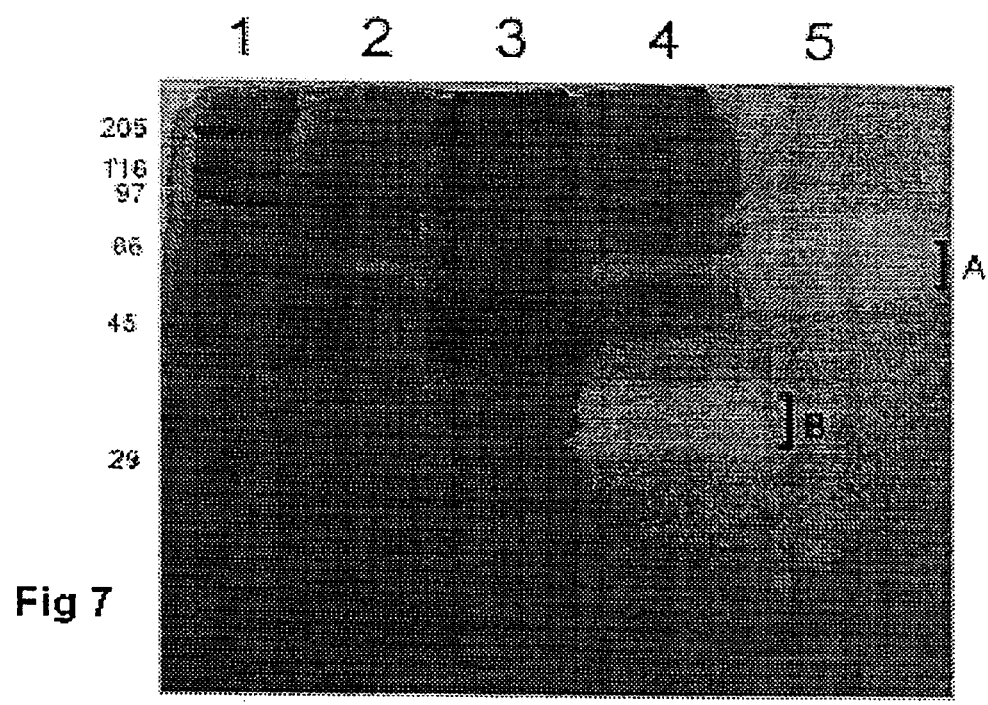

FIG. 7. Molecular weight determination of extracellular r-K2S harboring active serine protease domain by copolymerized plasminogen polyacrylamide gel electrophoresis. Lane 1 contained the indicated molecular weight standards ($\times 10^{-3}$), SDS-6H (Sigma, Saint Louis, Mo.). Fifty µg of the 55% saturated ammonium sulfate precipitated culture supernatant of XL-1 Blue, Xl-1 Blue transformed with pComb3HSS, and XM[K2S] were loaded in lane 2, 3, and 4 respectively. Lane 5 contained 50 mIU of standard melanoma tPA (86/670). Transparent zones of digested plasminogen in polyacrylamide gel are visible only in lane 4 at molecular weight of 34 and 37 kDa (B) and lane 5 at molecular weight of 66 and 72 kDa (A).

Figure 8:
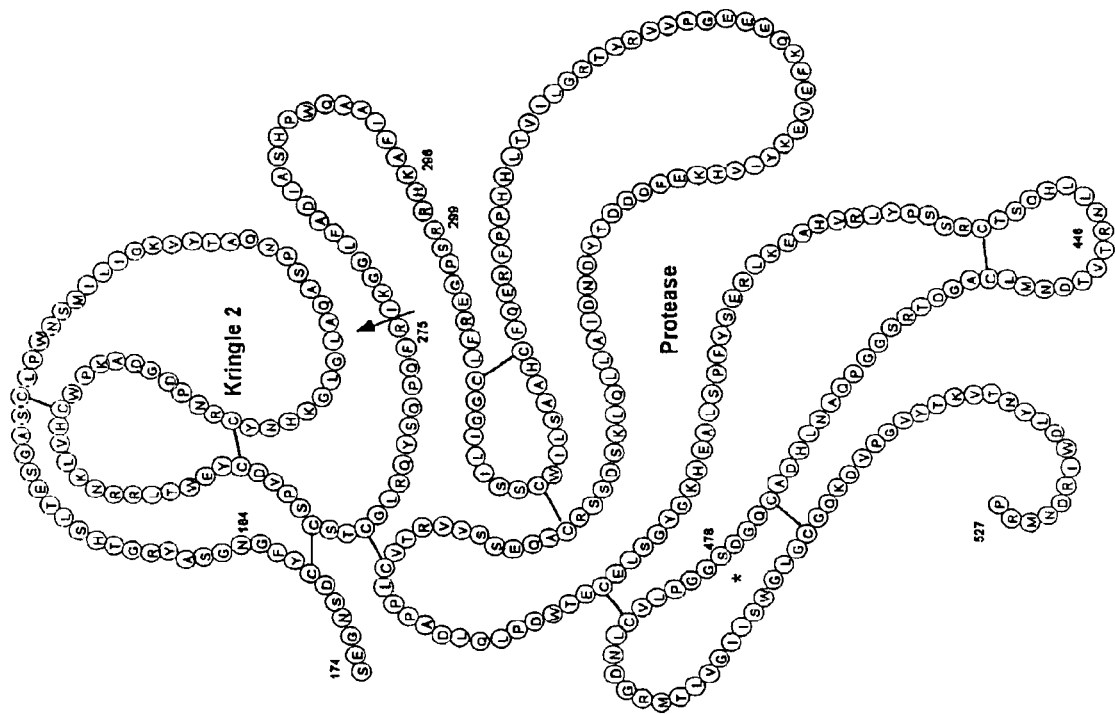

FIG. 8. Structure A (SEQ ID NO:11) Native K2S molecule from amino acids 174–527 without modification.

Figure 9:
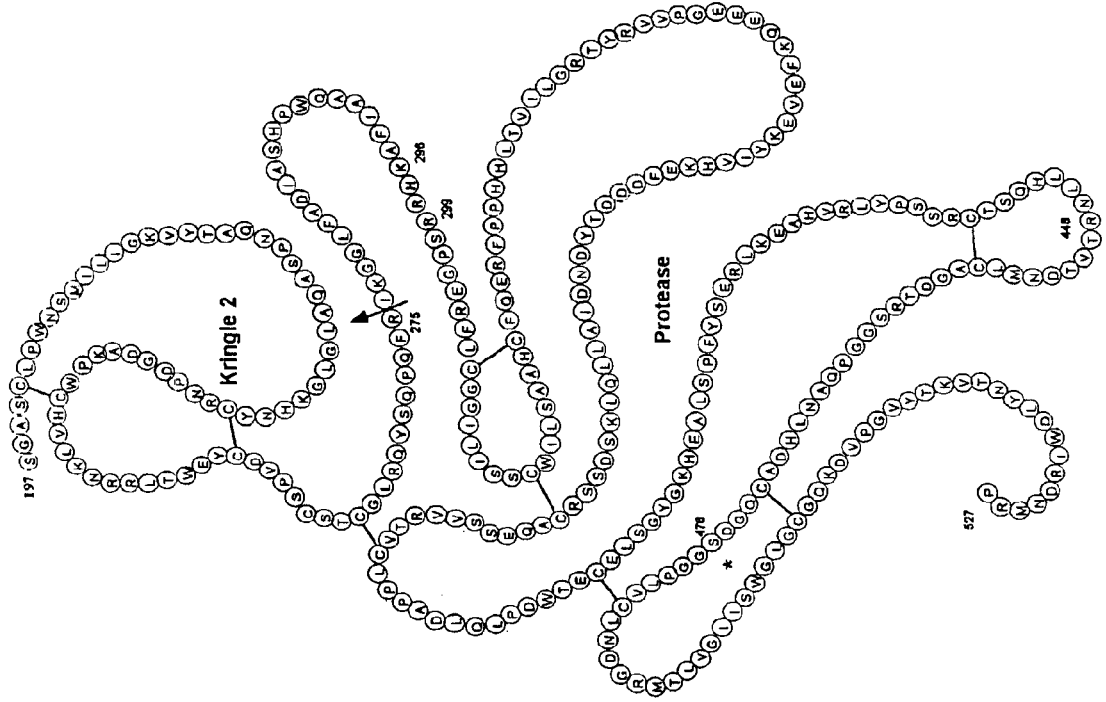

FIG. 9. Structure B-0 (SEQ ID NO:12) Native K2S molecule from amino acids 197–527 without modification.

Figure 10:
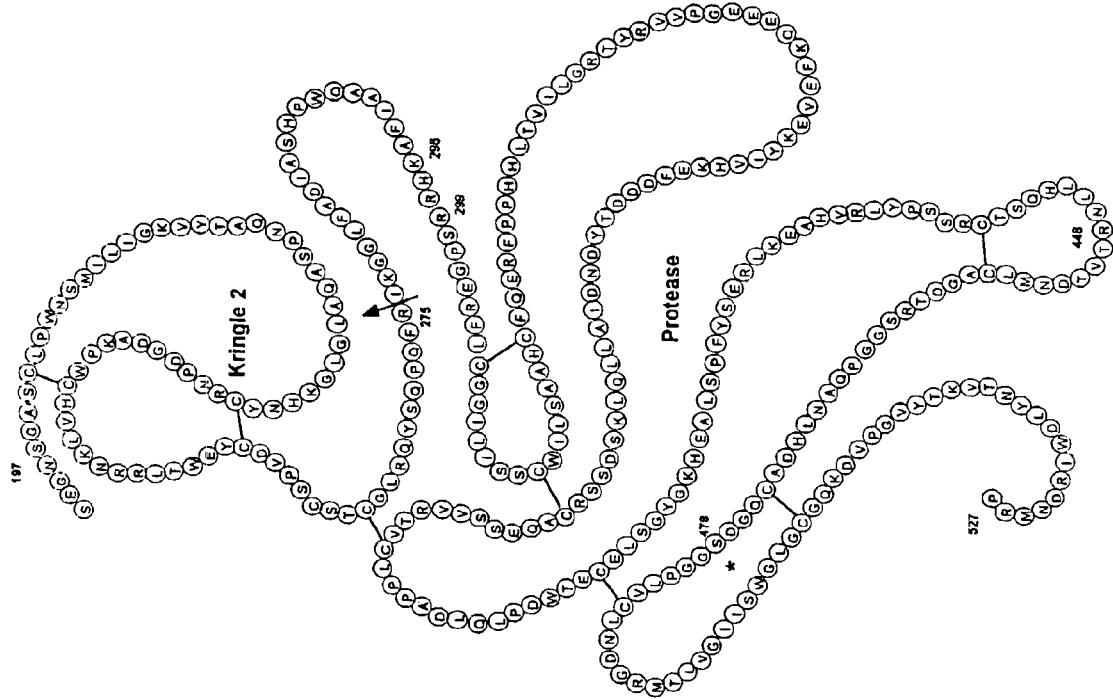

FIG. 10. Structure B-1 (SEQ ID NO:13) K2S molecule from amino acids 193–527, wherein to Structure B-0 of FIG. 9 the amino acids SEGN were added at the N-terminal portion.

Figure 11:
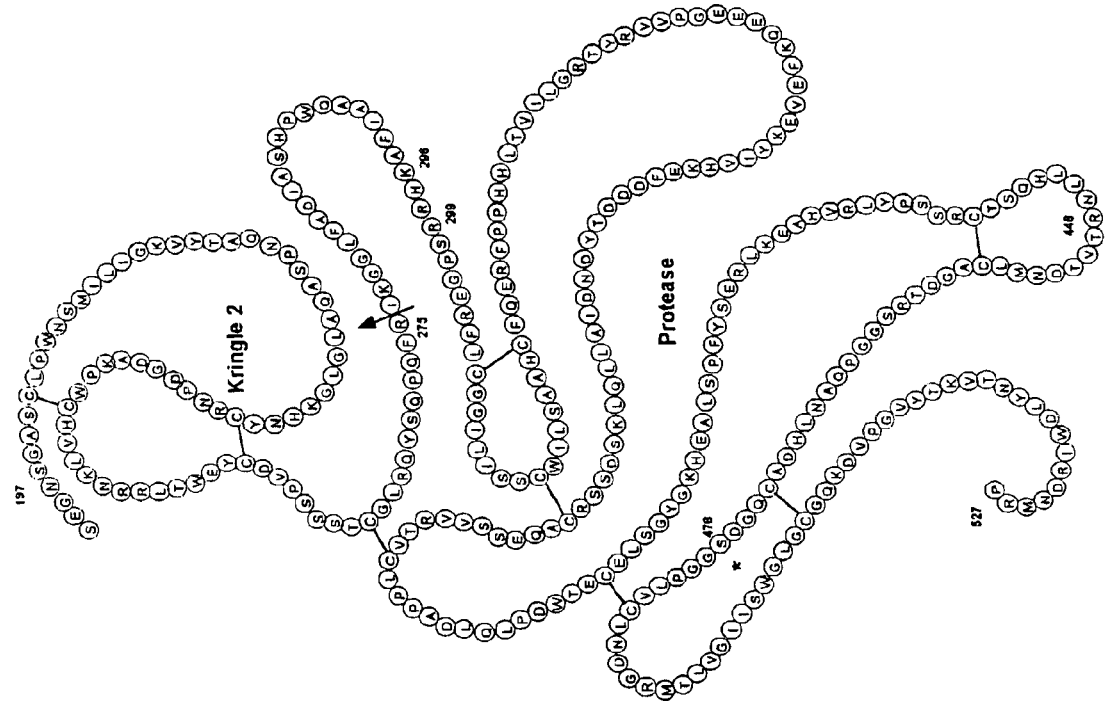

FIG. 11. Structure B-2 (SEQ ID NO:14) K2S molecule from amino acids 193–527, as in FIG. 10, wherein Cys-261 was exchanged for Ser.

Figure 12:
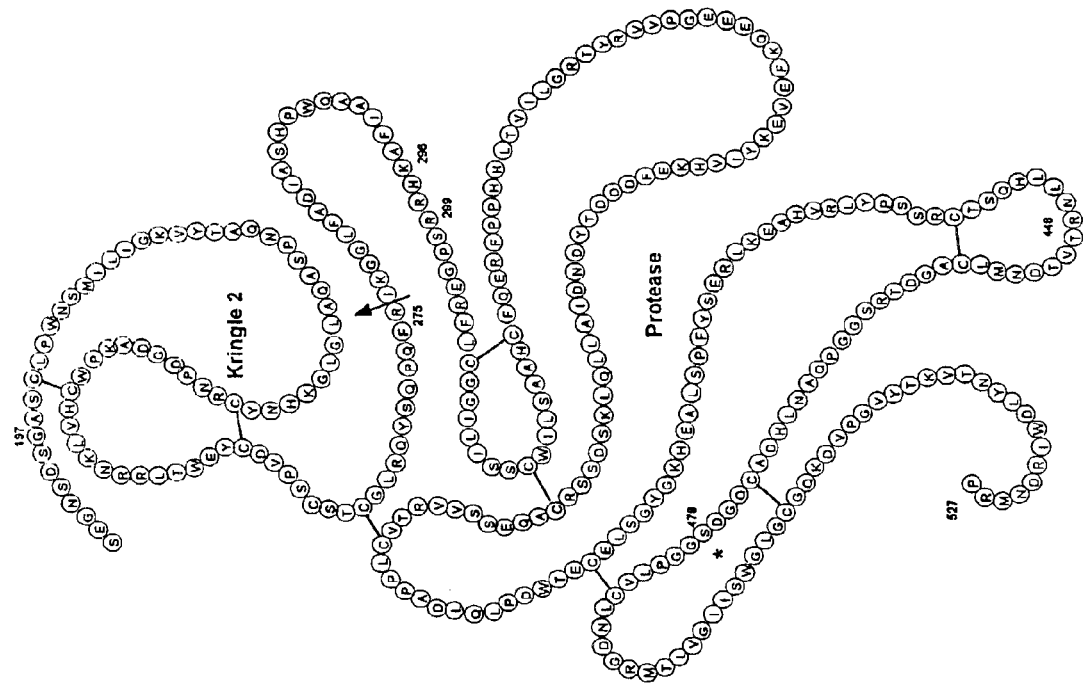

FIG. 12. Structure B-3 (SEQ ID NO:15) K2S molecule from amino acids 191–527, wherein to Structure B-0 of FIG. 9 the amino acids SEGNSD were added at the N-terminal portion.

Figure 13:
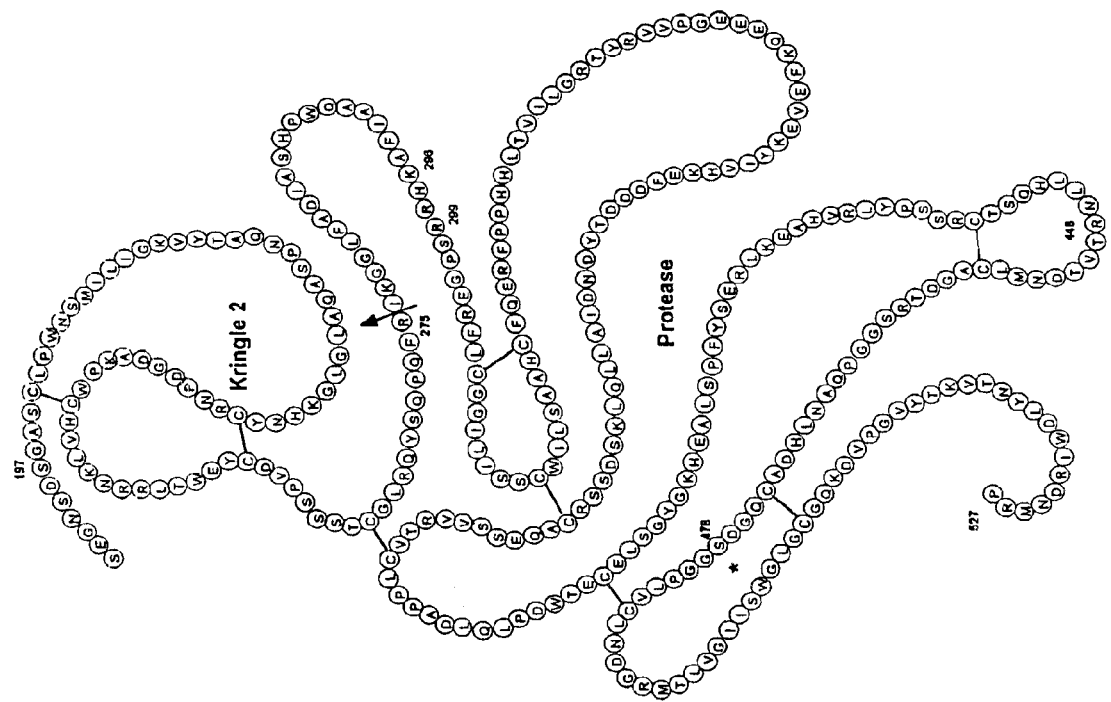

FIG. 13. Structure B-4 (SEQ ID NO:16) K2S molecule from amino acids 191–527, as in FIG. 12, wherein Cys-261 was exchanged for Ser.

Figure 14:
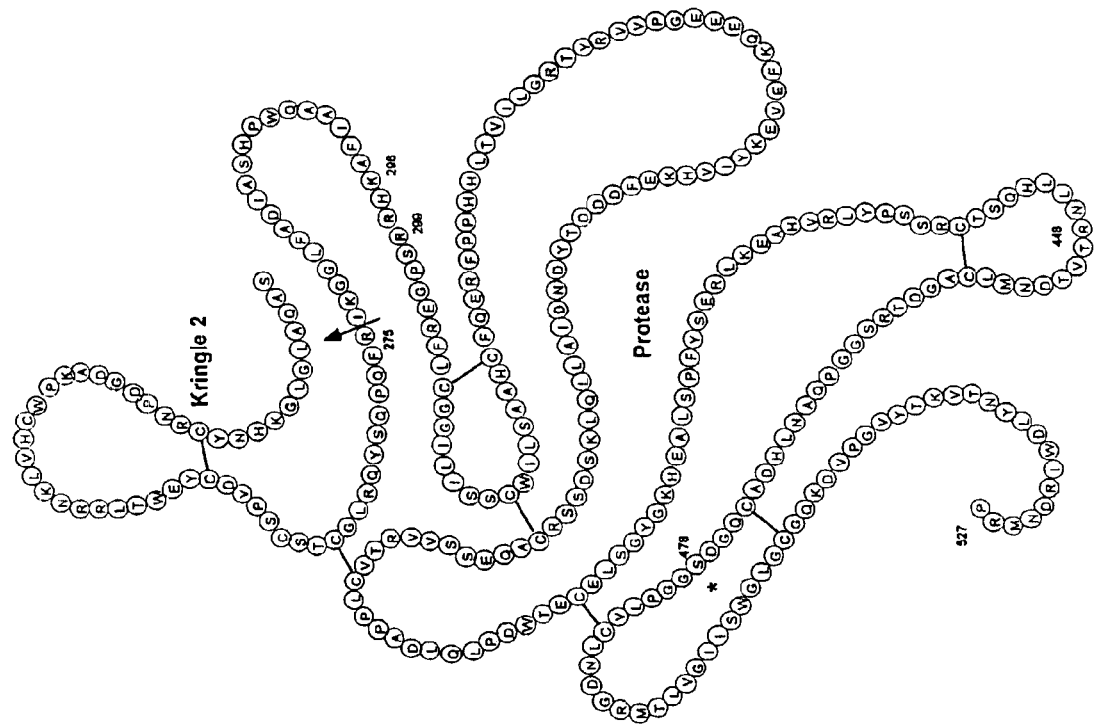

FIG. 14. Structure C (SEQ ID NO:17) Native K2S molecule from amino acids 220–527 without modification. This molecule may be further modified in a similar manner as disclosed for structure B in FIGS. 10–13.

Figure 15:
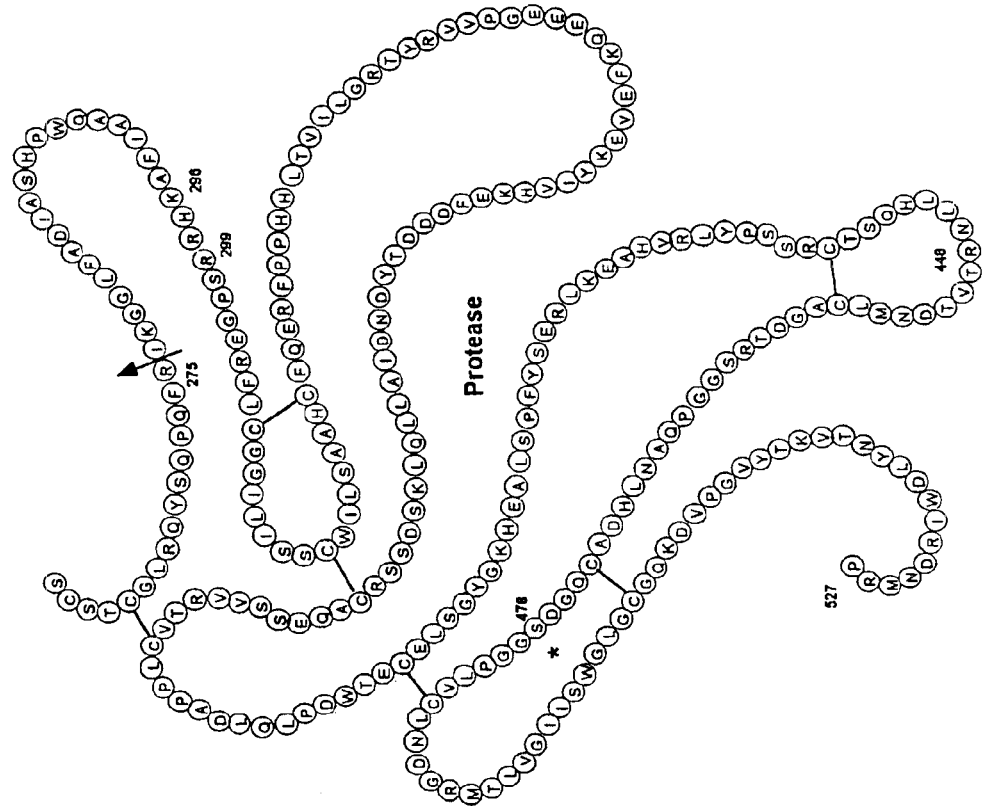

FIG. 15. Structure D (SEQ ID NO:18) Native K2S molecule from amino acids 260–527 without modification. This molecule may be further modified in a similar manner as disclosed for structure B in FIGS. 10–13.

Figure 16:
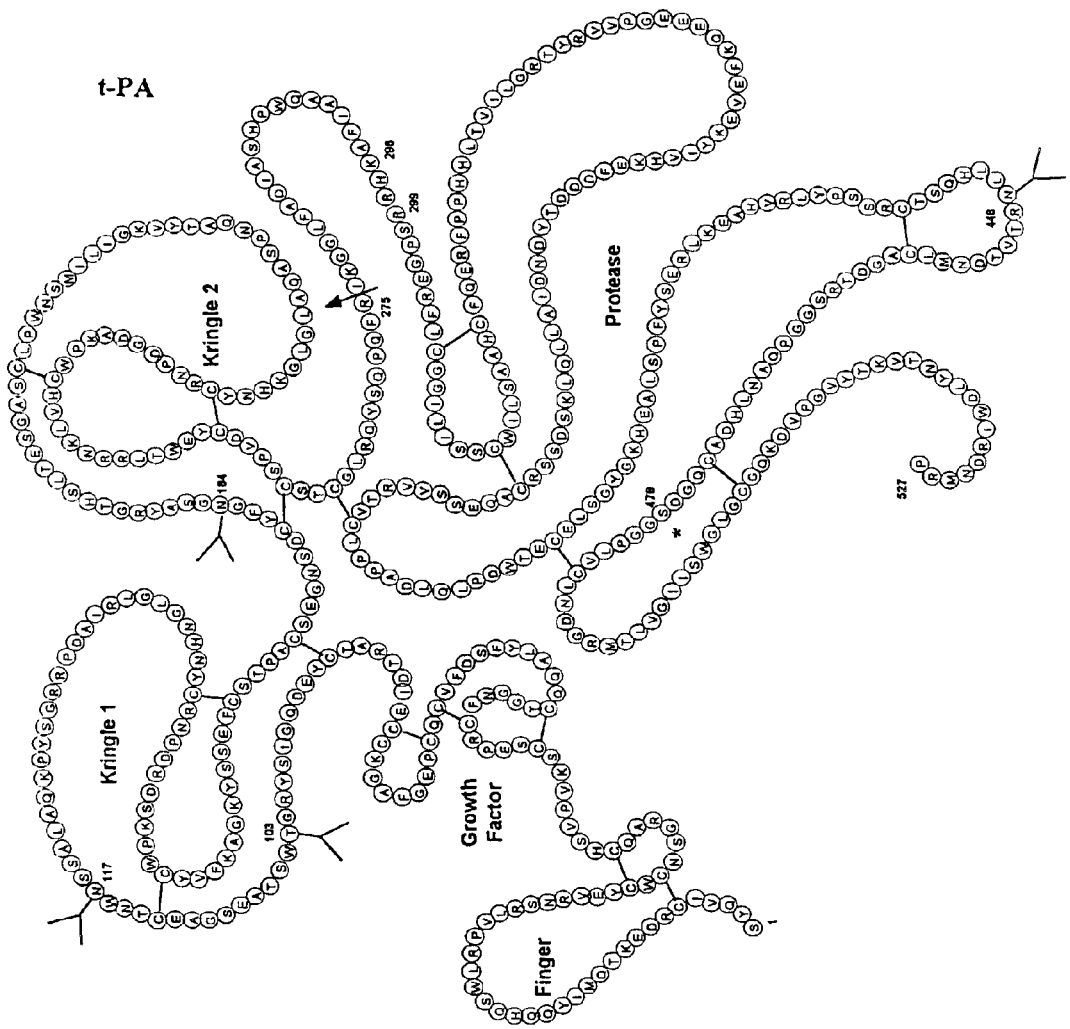

FIG. 16. tPA molecule (SEQ ID NO:19)

TABLE 1

DETECTION OF R-K2S MOLECULE IN PHAGE PREPARATION BY SANDWICH ELISA

| Capture antibody | Tracer antibody (conjugated HRP) | | | |
|---|---|---|---|---|
| | Anti-tPA | | Anti-M13 | |
| | K2S-φ | VCSM13[a] | K2S-φ | VCSM13 |
| Anti-kringle 2[b] | 1.12 ± 0.04[c] | 0.12 ± 0.03 | 1.89 ± 0.02 | 0.16 ± 0.02 |
| Anti-M13 | 0.17 ± 0.01 | 0.14 ± 0.05 | 1.91 ± 0.02 | 1.88 ± 0.03 |

[a]VCSM13 was harvested from XL-1 Blue transformed with pComb3HSS.
[b]Mouse monoclonal anti-kringle 2 (16/B) was used. The other antibodies were prepared from sheep immunoglobulin.
[c]Value is mean of absorbance of each sample which was assayed in triplicate.

DETAILED DESCRIPTION OF THE PREFERRED EMBODIMENTS

The use of the singular or plural in the claims or specification is in no way intended to be limiting and also includes the other form.

The invention relates to a method for the production of a recombinant DNA-derived tissue plasminogen activator (tPA), a tPA variant, a Kringle 2 Serine protease molecule (K2S) or a K2S variant in prokaryotic cells, wherein said tPA, tPA variant, K2S molecule or K2S variant is secreted extracellularly as an active and correctly folded protein, characterized in that the prokaryotic cell contains and expresses a vector comprising the DNA coding for said tPA, tPA variant, K2S molecule or K2S variant operably linked to the DNA coding for the signal peptide OmpA or a functional derivative thereof.

Surprisingly, the use of the signal peptide OmpA (SEQ ID NO:3) alone and/or in combination with the N-terminal amino acids SEGN (SEQ ID NO: 9)/SEGNSD (SEQ ID NO:10) translocate the recombinant DNA-derived tPA, tPA variant, K2S molecule or K2S variant to the outer surface and facilitates the release of the functional and active molecule into the culture medium to a greater extent than any other method in the prior art. Before crossing the outer membrane, the recombinant DNA-derived protein is correctly folded according to the method of the present invention. The signal peptide is cleaved off to produce a mature molecule. Surprisingly, the efficiency of signal peptide removal is very high and leads to correct folding of the recombinant DNA-derived protein.

Said signal peptide OmpA interacts with SecE and is delivered across the inner membrane by energy generated by SecA, which binds to Sec components (SecE-SecY). SecY forms a secretion pore to dispatch the recombinant DNA-derived protein according to the invention. The space between the outer membrane and inner membrane of Gram-negative bacteria, periplasm, has higher oxidative condition in comparison to the cytoplasmic space. This supports the formation of disulfide bonds and properly folding of the recombinant DNA-derived protein (e.g. K2S) in the periplasm to yield an active molecule. According to the present invention, the signal peptide will be cleaved off to produce a mature molecule. The complex of GspD secretin and GspS lipoprotein on the outer membrane serves as gate channel for secreting the recombinant DNA-derived protein according to the invention to the extracellular medium. This secretion process requires energy, which is generated in cytoplasm by GspE nucleotide-binding protein then transferred to the inner membrane protein (Gsp G-J, F and K-N). GspC transfers the energy to GspD by forming a cross-linker between a set of inner membrane protein (Gsp G-J, F and K-N) and GspD. Before crossing the outer membrane successfully, the recombinant DNA-derived protein is correctly folded.

Operably linked according to the invention means that the DNA encoding the tPA, tPA variant, K2S molecule or K2S variant (preferably comprising the nucleic acid encoding SEGN or SEGNSD at its N-terminal portion) is cloned in close proximity to the OmpA DNA into the vector in order to achieve expression of the OmpA-tPA, tPA variant, K2S molecule or K2S variant-fusion protein and to direct secretion outside the prokaryotic host cell. Typically, the majority of the tPA, tPA variant, K2S molecule or K2S variant is secreted and can then be purified by appropriate methods such as ammonium sulfate precipitation and/or affinity chromatography and further purification steps. The invention also includes the use of inducers such as IPTG or IPTG in combination with glycerol, the improvement of the incubation condition and harvesting period to maximize the amount of active protein.

In a preferred embodiment, said DNA encoding the OmpA signal peptide may be fused to a short peptide characterized by the amino acid sequence SEGN (SEQ ID NO:9) or SEGNSD (SEQ ID NO:10) or the coding nucleic acid sequence TCTGAGGGAAAC (SEQ ID NO:20) or TCTGAGGGAAACAGTGAC (SEQ ID NO:1) and located in the N-terminal portion or at the N-terminal portion of the tPA, tPA variant, K2S molecule or K2S variant. Thus, preferably, said fusion protein comprises OmpA-SEGNSD-tPA, -tPA-variant, -K2S-molecule or -K2S-variant. Even more preferred, said amino acids characterized by SEGN or SEGNSD may be carry a point mutation or may be substituted by a non-natural amino acid. Even more preferred, there may be an amino acid or non-amino acid spacer between OmpA and SEGN or SEGNSD and the tPA, tPA variant, K2S molecule or K2S variant.

Thus, in a preferred method according to the invention said the prokaryotic cell contains and expresses a vector comprising the DNA coding for said tPA, tPA variant, K2S molecule or K2S variant operably linked to the DNA coding for the signal peptide OmpA which is operably linked to the nucleic acid molecule defined by the sequence TCTGAGGGAAACAGTGAC(SEQ ID NO:11) or a functional derivative thereof.

The method according to the invention comprises prokaryotic host cells such as, but not limited to *Escherichia coli* (*E. coli*), *Bacillus subtilis*, *Streptomyces, Pseudomonas,* e.g. *Pseudomonas putida, Proteus mirabilis, Saccharomyces, Pichia* or *Staphylococcus*, e.g. *Staphylococcus carnosus*. Preferably said host cells according to the invention are Gram-negative bacteria.

Preferably, a method according to the invention is also characterised in that the prokaryotic cell is *E. coli*. Suitable strains include, but are not limited to *E. coli* XL-1 blue, BL21(DE3), JM109, DH series, TOP10 and HB101. Preferably, a method according to the invention is also characterised in that the following steps are carried out:

a) the DNA encoding the tPA, tPA variant, K2S molecule or K2S variant is amplified by PCR;

b) the PCR product is purified;

c) said PCR product is inserted into a vector comprising the DNA coding for OmpA signal peptide and the DNA coding for gpIII in such a way that said PCR product is operably linked upstream to the DNA coding for the OmpA signal sequence and linked downstream to the DNA coding for gpIII of said vector;

d) that a stop codon is inserted between said tPA, tPA variant, K2S molecule or K2S variant and gpIII;

e) said vector is expressed by the prokaryotic cell f) the tPA, tPA variant, K2S molecule or K2S variant is purified.

For step a) according to the invention the choice/design of the primers is important to clone the DNA in the right location and direction of the expression vector (see example 1). Thus, the primers as exemplified in example 1 and FIG. 4 comprise an important aspect of the present invention. With gp III of step c) gene protein III is meant which is present mainly in phagemid vectors. The stop codon is inserted to avoid transcription of gp III thus eventually leading to secretion of the tPA, tPA variant, K2S molecule or K2S variant of interest. Any suitable method for insertion of the stop codon may be employed such as site-directed mutagenesis (e.g., Weiner M P, Costa G L (1994) PCR Methods Appl 4(3):S131–136; Weiner M P, Costa G L, Schoettlin W, Cline J, Mathur E, Bauer J C (1994) Gene 151(1–2):119–123; see also example 1).

Any vector may be used in the method according to the invention, preferably said vector is a phagemid vector (see below).

Preferably, a method according to the invention is also characterised in that the tPA, tPA variant, K2S molecule or K2S variant is selected from human tissue plasminogen activator (tPA, FIG. 16) or a fragment, a functional variant, an allelic variant, a subunit, a chemical derivative, a fusion protein or a glycosylation variant therof. Such fragments, allelic variants, functional variants, variants based on the degenerative nucleic acid code, fusion proteins with an tPA protein according to the invention, chemical derivatives or a glycosylation variant of the tPA proteins according to the invention may include one, several or all of the following domains or subunits or variants thereof:

| | |
|---|---|
| 1. | Finger domain (4–50) |
| 2. | Growth factor domain (50–87) |
| 3. | Kringle 1 domain (87–176) |
| 4. | Kringle 2 domain (176–262) |
| 5. | Protease domain (276–527) |

The numbering/naming of the domains is according to Genbank accession number GI 137119 or Nature 301 (5897), 214–221 (1983).

More preferably, a method according to the invention is also characterised in that the tPA, tPA variant, K2S molecule or K2S variant is selected from the Kringle 2 (Barbas, C. F. III and Wagner, J., et al., *Enzymology* 8: 94–103 (1995)) plus Serine protease (Bennett, W. F., et al., *J Biol Chem.* 266:5191–5201 (1991)) K2S variant of human tissue plasminogen activator or a fragment, a functional variant, an allelic variant, a subunit, a chemical derivative, a fusion protein or a glycosylation variant therof.

More preferably, a method according to the invention is also characterised in that the vector is a phagemid vector comprising the DNA coding for OmpA signal peptide and the DNA coding for gpIII.

More preferably, a method according to the invention is also characterised in that the vector is the pComb3HSS phagemid (see also example 1).

More preferably, a method according to the invention is also characterised in that the DNA sequence comprises or consists of the following DNA sequence encoding OmpA and K2S or a functional variant thereof or a variant due to the degenerate nucleotide code:

```
                                               (SEQ ID NO:2)
ATGAAAAAGACAGCTATCGCGATTGCAGTGGCACTGGCTGGTTTCG

CTACCGTGGCCCAGGCGGCCTCTGAGGGAAACAGTGACTGCTACTT

TGGGAATGGGTCAGCCTACCGTGGCACGCACAGCCTCACCGAGTCG

GGTGCCTCCTGCCTCCCGTGGAATTCCATGATCCTGATAGGCAAGG

TTTACACAGCACAGAACCCAGTGCCCAGGCACTGGGCCTGGGCA

AACATAATTACTGCCGGAATCCTGATGGGGATGCCAAGCCCTGGTG

CCACGTGCTGAAGAACCGCAGGCTGACGTGGGAGTACTGTGATGT

GCCCTCCTGCTCCACCTGCGGCCTGAGACAGTACAGCCAGCCTCAG

TTTCGCATCAAAGGAGGGCTCTTCGCCGACATCGCCTCCCACCCCT

GGCAGGCTGCCATCTTTGCCAAGCACAGGAGGTCGCCCGGAGAGC

GGTTCCTGTGCGGGGGCATACTCATCAGCTCCTGCTGGATTCTCTCT

GCCGCCCACTGCTTCCAGGAGAGGTTTCCGCCCCACCACCTGACGG

TGATCTTGGGCAGAACATACCGGGTGGTCCCTGGCGAGGAGGAGC

AGAAATTTGAAGTCGAAAAATACATTGTCCATAAGGAATTCGATGA

TGACACTTACGACAATGACATTGCGCTGCTGCAGCTGAAATCGGAT

TCGTCCCGCTGTGCCCAGGAGAGCAGCGTGGTCCGCACTGTGTGCC

TTCCCCCGGCGGACCTGCAGCTGCCGGACTGGACGGAGTGTGAGCT

CTCCGGCTACGGCAAGCATGAGGCCTTGTCTCCTTTCTATTCGGAG

CGGCTGAAGGAGGCTCATGTCAGACTGTACCCATCCAGCCGCTGCA
```

CATCACAACATTTACTTAACAGAACAGTCACCGACAACATGCTGTG

TGCTGGAGACACTGGGAGCGGCGGGCCCCAGGCAAACTTGCACGA

CGCCTGCCAGGGCGATTCGGGAGGCCCCCTGGTGTGTCTGAACGAT

GGCCGCATGACTTTGGTGGGCATCATCAGCTGGGGCCTGGGCTGTG

GACAGAAGGATGTCCCGGGTGTGTACACAAAGGTTACCAACTACCT

AGACTGGATTCGTGACAACATGCGACCG

More preferably, a method according to the invention is also characterised in that the DNA Sequence of OmpA comprises or consists of the following sequence or a functional variant thereof or a variant due to the degenerate nucleotide code:

ATGAAAAAGACAGCTATCGCGATTGCAGTGGCACTGGCTGGTTTCG

CTACCGTGGCCCAGGCGGCC (SEQ ID NO:3).

Said DNA encodes the following amino acid sequence of OmpA. OmpA thus comprises or consists of a protein characterized by the following amino acid sequence or a fragment, a functional variant, an allelic variant, a subunit, a chemical derivative or a glycosylation variant therof as part of the invention:

MKKTAIAIAVALAGFATVAQAA (SEQ ID NO:21).

The untranslated region may contain a regulatory element, such as e.g. a transcription initiation unit (promoter) or enhancer. Said promoter may, for example, be a constitutive, inducible or development-controlled promoter. Preferably, without ruling out other known promoters, the constitutive promoters of the human Cytomegalovirus (CMV) and Rous sarcoma virus (RSV), as well as the Simian virus 40 (SV40) and Herpes simplex promoter. Inducible promoters according to the invention comprise antibiotic-resistant promoters, heat-shock promoters, hormone-inducible "Mammary tumour virus promoter" and the metallothioneine promoter. Preferred promotors include the T3 promotor, T7 promotor, Lac/aral and Ltet0-1.

More preferably, a method according to the invention is also characterised in that the DNA of the tPA, tPA variant, K2S molecule or K2S variant is preceeded by a lac promotor and/or a ribosomal binding site such as the Shine-Dalgarno sequence (see also example).

More preferably, a method according to the invention is also characterized in that the DNA coding for the LPA, tPA variant, K25 molecule or K25 variant is selected from the group of DNA molecules coding for at least 90% of the amino acids 87–527, 174–527, 180–527 or 220–527 of the human tissue plasminogen activator protein (SEQ ID NO:19).

More preferably, a method according to the invention is also characterised in that the DNA Sequence of K2S comprises or consists of the following sequence:

TCTGAGGGAAACAGTGACTGCTACTTTGGGAATGGGTCAGCCTACC

GTGGCACGCACAGCCTCACCGAGTCGGGTGCCTCCTGCCTCCCGTG

GAATTCCATGATCCTGATAGGCAAGGTTTACACAGCACAGAACCCC

AGTGCCCAGGCACTGGGCCTGGGCAAACATAATTACTGCCGGAATC

-continued
```
CTGATGGGGATGCCAAGCCCTGGTGCCACGTGCTGAAGAACCGCA

GGCTGACGTGGGAGTACTGTGATGTGCCCTCCTGCTCCACCTGCGG

CCTGAGACAGTACAGCCAGCCTCAGTTTCGCATCAAAGGAGGGCTC

TTCGCCGACATCGCCTCCCACCCCTGGCAGGCTGCCATCTTTGCCA

AGCACAGGAGGTCGCCCGGAGAGCGGTTCCTGTGCGGGGCATAC

TCATCAGCTCCTGCTGGATTCTCTCTGCCGCCCACTGCTTCCAGGAG

AGGTTTCCGCCCCACCACCTGACGGTGATCTTGGGCAGAACATACC

GGGTGGTCCCTGGCGAGGAGGAGCAGAAATTTGAAGTCGAAAAAT

ACATTGTCCATAAGGAATTCGATGATGACACTTACGACAATGACAT

TGCGCTGCTGCAGCTGAAATCGGATTCGTCCCGCTGTGCCCAGGAG

AGCAGCGTGGTCCGCACTGTGTGCCTTCCCCCGGCGGACCTGCAGC

TGCCGGACTGGACGGAGTGTGAGCTCTCCGGCTACGGCAAGCATG

AGGCCTTGTCTCCTTTCTATTCGGAGCGGCTGAAGGAGGCTCATGT

CAGACTGTACCCATCCAGCCGCTGCACATCACAACATTTACTTAAC

AGAACAGTCACCGACAACATGCTGTGTGCTGGAGACACTCGGAGC

GGCGGGCCCCAGGCAAACTTGCACGACGCCTGCCAGGGCGATTCG

GGAGGCCCCCTGGTGTGTCTGAACGATGGCCGCATGACTTTGGTGG

GCATCATCAGCTGGGGCCTGGGCTGTGGACAGAAGGATGTCCCGG

GTGTGTACACAAAGGTTACCAACTACCTAGACTGGATTCGTGACAA

CATGCGACCGTGA (SEQ ID NO:4).
```

The present invention also relates to variants of the before-mentioned nucleic acid molecules due to the degenerate code or to fragments therof, nucleic acids which hybridize to said nucleic acids under stringent conditions, allelic or functional variants. The invention also relates to nucleic acids comprising said K2S nucleic acid fused to the nucleic acid encoding another protein molecule.

Stringent conditions as understood by the skilled person are conditions which select for more than 85%, preferred more than 90% homology (Sambrook et al. 1989; Molecular Cloning: A Laboratory Manual, 2$^{nd}$ ed., Cold Spring Harbor Laboratory Press, Cold Spring Harbor, N.Y.). The hybridisation will be carried out e.g. in 6×SSC/5× Denhardt's solution/0,1% SDS (SDS: sodium dodecylsulfate) at 65° C. The degree of stringency is decided in the washing step. Thus, for example for a selection of DNA-sequences with approx. 85% or more homology, the conditions 0,2×SSC/ 0.01% SDS/65° C. and for a selection of DNA-sequences of approx. 90% or more homology the conditions 0.1×SSC/ 0.01% SDS/65° C. are suitable. The composition of said reagents is described in Sambrook et al. (1989, supra).

Another important part of the present invention is a variant of human tissue plasminogen activator comprising of or consisting of the Kringle 2 (Barbas, C. F. III and Wagner, J., et al., *Enzymology* 8: 94–103 (1995)) plus Serine protease (Bennett, W. F., et al., *J Biol Chem.* 266:5191–5201 (1991)) (abbreviated K2S) protein or a variant or a fragment, a functional variant, an allelic variant, a subunit, a chemical derivative, a fusion protein or a glycosylation variant therof.

The numbering/naming of the domains is according to Genbank accession number GI 137119 or Nature 301 (5897), 214–221 (1983), wherein the Kringle 2 domain extends from amino acid 176–262 and the protease domain from 276–527. Thus, according to the invention, a preferred K2S molecule may include amino acids 176–527 including the amino acids between Kringle 2 and the protease (amino acids 263 to 275; exemplified in FIG. 8 (structure A)). A K2S molecule according to the invention comprises the minimal part of the Kringle 2 domain and the protease domain still retaining protease activity and fibrin binding activity (measured as exemplified in the description/example). Said K2S molecule according to the invention comprises the amino acids SEGN or SEGNSD in its N-terminal portion (see infra). A preferred K2S molecule does not include amino acids 1 to 3 or 1 to 5 of the tPA molecule. Preferably, a K2S molecule according to the invention has the amino acid Asn at positions 177 and 184, i.e. it does not require the modifications as disclosed in Waldenström for improved producibility with a method according to the invention. Thus, a preferred K2S molecule according to the invention has the native amino acid sequence (no mutation) as opposed to the molecules known from the prior art. Most preferred, said K2S molecule according to the invention is a molecule characterized by the native amino acid sequence or parts thereof, does neither have amino acids 1 to 3 nor 1 to 5 of tPA and comprises N-terminally the amino acids SEGN or SEGNSD for improved producibility and/or correct folding of the molecule.

It is essential that the K2S protein according to the invention comprises in its N-terminal portion a peptide characterized by the amino acid sequence SEGN which advantageously allows commercial production with a method as described supra leading to a correctly folded, secreted K2S protein. Said 4 amino acids characterized by SEGN may have one or several amino acids more N-terminal, however said amino acids have to be located in the N-terminal portion as opposed to the C-terminal portion. Most preferably, said amino acids are located at the N-terminal portion. Preferably, the amino acids characterized by SEGN may be carry a point mutation or may be substituted by a non-natural amino acid.

Thus, in another important embodiment the invention relates to a K2S protein characterized in that it comprises the amino acids defined by the sequence SEGN or a variant or a fragment, a functional variant, an allelic variant, a subunit, a chemical derivative, a fusion protein or a glycosylation variant therof.

Such fragments are exemplified e.g. in FIG. 10 (Structure B-1) and FIG. 11 (Structure B-2) extending from amino acids 193–527. Structure B-1 has the native amino acid Cys in position 261, wherein in B-2 the amino acid is substituted by Ser. Further fragments according to the invention comprising the amino acids 220–527 (FIG. 14, structure C) or comprising the amino acids 260–527 (FIG. 15, structure D) may be modified according to the invention by addition of the amino acids SEGN and/or substitution of Cys-261 by Ser. The artisan can determine the minimal length of a K2S molecule according to the invention in order to retain its biological function and generate a K2S molecule with improved producibility and/or correct folding by adding the amino acids SEGN in the N-terminal portion. Thus, another preferred embodiment is said minimal K2S molecule with SEGN at its N-terminal portion.

In another important embodiment the invention relates to a K2S protein characterized in that it comprises the amino acids defined by the sequence SEGNSD or a variant or a fragment, a functional variant, an allelic variant, a subunit, a chemical derivative, a fusion protein or a glycosylation variant therof. Such fragments are exemplified e.g. in FIG. 12 (Structure B-3) and FIG. 13 (Structure B-4) extending from amino acids 191–527. Structure B-3 has the native amino acid Cys in position 261, wherein in B-4 the amino acid is substituted by Ser. Further fragments according to the invention comprising the amino acids 220–527 (FIG. 14, structure C) or comprising the amino acids 260–527 (FIG. 15, structure D) may be modified according to the invention by addition of the amino acids SEGNSD and/or substitution of Cys-261 by Ser. The artisan can determine the minimal length of a K2S molecule according to the invention in order to retain its biological function and generate a K2S molecule with improved producibility and/or correct folding by adding the amino acids SEGNSD in the N-terminal portion. Thus, another preferred embodiment is said minimal K2S molecule with SEGNSD at its N-terminal portion.

Another more preferred embodiment of the present invention relates to a K2S protein comprising a protein characterized by the following amino acid sequence or a variant or a fragment, a functional variant, an allelic variant, a subunit, a chemical derivative or a glycosylation variant therof:

SEGNSDCYFGNGSAYRGTHSLTESGASCLPWNSMILIGKVYTAQNPSA

QALGLGKHNYCRNPDGDAKPWCHVLKNRRLTWEYCDVPSCSTCGLR

QYSQPQFRIKGGLFADIASHPWQAAIFAKHRRSPGERFLCGGILISSCWI

LSAAHCFQERFPPHHLTVILGRTYRVVPGEEEQKFEVEKYIVHKEFDD

DTYDNDIALLQLKSDSSRCAQESSVVRTVCLPPADLQLPDWTECELSG

YGKHEALSPFYSERLKEAHVRLYPSSRCTSQHLLNRTVTDNMLCAGD

TRSGGPQANLHDACQGDSGGPLVCLNDGRMTLVGIISWGLGCGQKD

VPGVYTKVTNYLDWIRDNMRP* (SEQ ID NO:11).

According to the invention, * means STOP (i.e. encoded by a stop codon). This K2S molecule is exemplified in FIG. 8.

One variant of the K2S molecule according to the invention relates to a fusion protein of K2S being fused to another protein molecule.

Another more preferred embodiment of the present invention relates to a K2S protein consisting of a protein characterized by the following amino acid sequence:

SEGNSDCYFGNGSAYRGTHSLTESGASCLPWNSMILIGKVYTAQNPSA

QALGLGKHNYCRNPDGDAKPWCHVLKNRRLTWEYCDVPSCSTCGLR

QYSQPQFRIKGGLFADIASHPWQAAIFAKHRRSPGERFLCGGILISSCWI

LSAAHCFQERFPPHHLTVILGRTYRVVPGEEEQKFEVEKYIVHKEFDD

DTYDNDIALLQLKSDSSRCAQESSVVRTVCLPPADLQLPDWTECELSG

YGKHEALSPFYSERLKEAHVRLYPSSRCTSQHLLNRTVTDNMLCAGD

TRSGGPQANLHDACQGDSGGPLVCLNDGRMTLVGIISWGLGCGQKD

VPGVYTKVTNYLDWIRDNMRP* (SEQ ID NO:11).

Said K2S molecules may be encoded by a DNA molecule as described supra.

Another important aspect of the invention relates to a DNA molecule characterized in that it is coding for:

a) the OmpA protein or a functional derivative therof operably linked to b) a DNA molecule coding for a polypeptide containing the kringle 2 domain and the serine protease domain of tissue plasminogen activator protein.

More preferably, a DNA molecule according to the invention is also characterised in that the DNA sequence comprises or consists of the following DNA sequence encoding OmpA and K2S or a functional variant thereof or a variant due to the degenerate nucleotide code:

(SEQ ID NO:2)
ATGAAAAAGACAGCTATCGCGATTGCAGTGGCACTGGCTGGTTTCG

CTACCGTGGCCCAGGCGGCCTCTGAGGGAAACAGTGACTGCTACTT

TGGGAATGGGTCAGCCTACCGTGGCACGCACAGCCTCACCGAGTCG

GGTGCCTCCTGCCTCCCGTGGAATTCCATGATCCTGATAGGCAAGG

TTTACACAGCACAGAACCCCAGTGCCCAGGCACTGGGCCTGGGCA

AACATAATTACTGCCGGAATCCTGATGGGGATGCCAAGCCCTGGTG

CCACGTGCTGAAGAACCGCAGGCTGACGTGGGAGTACTGTGATGT

GCCCTCCTGCTCCACCTGCGGCCTGAGACAGTACAGCCAGCCTCAG

TTTCGCATCAAAGGAGGGCTCTTCGCCGACATCGCCTCCCACCCCT

GGCAGGCTGCCATCTTTGCCAAGCACAGGAGGTCGCCCGGAGAGC

GGTTCCTGTGCGGGGGCATACTCATCAGCTCCTGCTGGATTCTCTCT

GCCGCCCACTGCTTCCAGGAGAGGTTTCCGCCCCACCACCTGACGG

TGATCTTGGGCAGAACATACCGGGTGGTCCCTGGCGAGGAGGAGC

AGAAATTTGAAGTCGAAAAATACATTGTCCATAAGGAATTCGATGA

TGACACTTACGACAATGACATTGCGCTGCTGCAGCTGAAATCGGAT

TCGTCCCGCTGTGCCCAGGAGAGCAGCGTGGTCCGCACTGTGTGCC

TTCCCCCGGCGGACCTGCAGCTGCCGGACTGGACGGAGTGTGAGCT

CTCCGGCTACGGCAAGCATGAGGCCTTGTCTCCTTTCTATTCGGAG

CGGCTGAAGGAGGCTCATGTCAGACTGTACCCATCCAGCCGCTGCA

CATCACAACATTTACTTAACAGAACAGTCACCGACAACATGCTGTG

TGCTGGAGACACTCGGAGCGGCGGGCCCCAGGCAAACTTGCACGA

CGCCTGCCAGGGCGATTCGGGAGGCCCCCTGGTGTGTCTGAACGAT

GGCCGCATGACTTTGGTGGGCATCATCAGCTGGGGCCTGGGCTGTG

GACAGAAGGATGTCCCGGGTGTGTACACAAAGGTTACCAACTACCT

AGACTGGATTCGTGACAACATGCGACCG

Said DNA molecule encodes the following fusion protein of OmpA and K2S. Said fusion protein of OmpA and K2S characterised in that it comprises or consists of a protein characterized by the following amino acid sequence or a fragment, a functional variant, an allelic variant, a subunit, a chemical derivative or a glycosylation variant therof forms an important part of the present invention:

(SEQ ID NO:8)
MKKTAIAIAVALAGFATVAQAASEGNSDCYFGNGSAYRGTHSLTESG

ASCLPWNSMILIGKVYTAQNPSAQALGLGKHNYCRNPDGDAKPWCH

VLKNRRLTWEYCDVPSCSTCGLRQYSQPQFRIKGGLFADIASHPWQA

AIFAKHRRSPGERFLCGGILISSCWILSAAHCFQERFPPHHLTVILGRTY

RVVPGEEEQKFEVEKYIVHKEFDDDTYDNDIALLQLKSDSSRCAQESS

VVRTVCLPPADLQLPDWTECELSGYGKHEALSPFYSERLKEAHVRLYP

SSRCTSQHLLNRTVTDNMLCAGDTRSGGPQANLHDACQGDSGGPLVC

LNDGRMTLVGIISWGLGCGQKDVPGVYTKVTNYLDWIRDNMRPG

Another preferred aspect of the invention relates to a DNA molecule according to the invention, characterized in that said DNA sequence b) is coding for at least 90% of the amino acids 87–527 of the human tissue plasminogen activator protein (numbering used herein as GI 137119 or Nature 301 (5897), 214–221 (1983).

Another preferred aspect of the invention relates to a DNA molecule according to the invention, characterized in that said DNA sequence b) is coding for at least 90% of the amino acids 174–527 of the human tissue plasminogen activator protein.

Another preferred aspect of the invention relates to a DNA molecule according to the invention, characterized in that said DNA sequence b) is coding for at least 90% of the amino acids 180–527 of the human tissue plasminogen activator protein.

Another preferred aspect of the invention relates to a DNA molecule according to the invention, characterized in that said DNA sequence b) is coding for at least 90% of the amino acids 220–527 of the human tissue plasminogen activator protein.

Another preferred aspect of the invention relates to a DNA molecule according to the invention, characterized in that said DNA sequence a) is hybridizing under stringent conditions to the following sequence:

ATGAAAAAGACAGCTATCGCGATTGCAGTGGCACTGGCTGGTTTCG

CTACCGTGGCCCAGGCGGCC (SEQ ID NO:3).

Another preferred aspect of the invention relates to a DNA molecule according to the invention, characterized in that said DNA sequence a) consists of the following sequence:

ATGAAAAAGACAGCTATCGCGATTGCAGTGGCACTGGCTGGTTTCG

CTACCGTGGCCCAGGCGGCC (SEQ ID NO:3).

Another preferred aspect of the invention relates to a DNA molecule according to the invention, characterized in that said DNA sequence b) is hybridizing under stringent conditions to the following sequence:

TCTGAGGGAAACAGTGACTGCTACTTTGGGAATGGGTCAGCCTACC

GTGGCACGCACAGCCTCACCGAGTCGGGTGCCTCCTGCCTCCCGTG

GAATTCCATGATCCTGATAGGCAAGGTTTACACAGCACAGAACCCC

AGTGCCCAGGCACTGGGCCTGGGCAAACATAATTACTGCCGGAATC

CTGATGGGGATGCCAAGCCCTGGTGCCACGTGCTGAAGAACCGCA

GGCTGACGTGGGAGTACTGTGATGTGCCCTCCTGCTCCACCTGCGG

CCTGAGACAGTACAGCCAGCCTCAGTTTCGCATCAAAGGAGGGCTC

TTCGCCGACATCGCCTCCCACCCCTGGCAGGCTGCCATCTTTGCCA

AGCACAGGAGGTCGCCCGGAGAGCGGTTCCTGTGCGGGGGCATAC

TCATCAGCTCCTGCTGGATTCTCTCTGCCGCCCACTGCTTCCAGGAG

AGGTTTCCGCCCCACCACCTGACGGTGATCTTGGGCAGAACATACC

GGGTGGTCCCTGGCGAGGAGGAGCAGAAATTTGAAGTCGAAAAAT

ACATTGTCCATAAGGAATTCGATGATGACACTTACGACAATGACAT

TGCGCTGCTGCAGCTGAAATCGGATTCGTCCCGCTGTGCCCAGGAG

AGCAGCGTGGTCCGCACTGTGTGCCTTCCCCCGGCGGACCTGCAGC

TGCCGGACTGGACGGAGTGTGAGCTCTCCGGCTACGGCAAGCATG

AGGCCTTGTCTCCTTTCTATTCGGAGCGGCTGAAGGAGGCTCATGT

CAGACTGTACCCATCCAGCCGCTGCACATCACAACATTTACTTAAC

AGAACAGTCACCGACAACATGCTGTGTGCTGGAGACACTCGGAGC

GGCGGGCCCCAGGCAAACTTGCACGACGCCTGCCAGGGCGATTCG

GGAGGCCCCTGGTGTGTCTGAACGATGGCCGCATGACTTTGGTGG

GCATCATCAGCTGGGGCCTGGGCTGTGGACAGAAGGATGTCCCGG

GTGTGTACACAAAGGTTACCAACTACCTAGACTGGATTCGTGACAA

CATGCGACCGTGA (SEQ ID NO:4).

Another preferred aspect of the invention relates to a DNA molecule according to the invention, characterized in that said DNA sequence b) consists of the following sequence:

TCTGAGGGAAACAGTGACTGCTACTTTGGGAATGGGT (SEQ ID NO:4)

CAGCCTACCGTGGCACGCACAGCCTCACCGAGTCGGG

TGCCTCCTGCCTCCCGTGGAATTCCATGATCCTGATA

GGCAAGGTTTACACAGCACAGAACCCCAGTGCCCAGG

CACTGGGCCTGGGCAAACATAATTACTGCCGGAATCC

TGATGGGGATGCCAAGCCCTGGTGCCACGTGCTGAAG

AACCGCAGGCTGACGTGGGAGTACTGTGATGTGCCCT

CCTGCTCCACCTGCGGCCTGAGACAGTACAGCCAGCC

TCAGTTTCGCATCAAAGGAGGGCTCTTCGCCGACATC

GCCTCCCACCCCTGGCAGGCTGCCATCTTTGCCAAGC

ACAGGAGGTCGCCCGGAGAGCGGTTCCTGTGCGGGGG

CATACTCATCAGCTCCTGCTGGATTCTCTCTGCCGCC

CACTGCTTCCAGGAGAGGTTTCCGCCCCACCACCTGA

CGGTGATCTTGGGCAGAACATACCGGGTGGTCCCTGG

CGAGGAGGAGCAGAAATTTGAAGTCGAAAAATACATT

GTCCATAAGGAATTCGATGATGACACTTACGACAATG

ACATTGCGCTGCTGCAGCTGAAATCGGATTCGTCCCG

CTGTGCCCAGGAGAGCAGCGTGGTCCGCACTGTGTGC

CTTCCCCCGGCGGACCTGCAGCTGCCGGACTGGACGG

AGTGTGAGCTCTCCGGCTACGGCAAGCATGAGGCCTT

GTCTCCTTTCTATTCGGAGCGGCTGAAGGAGGCTCAT

GTCAGACTGTACCCATCCAGCCGCTGCACATCACAAC

-continued

ATTTACTTAACAGAACAGTCACCGACAACATGCTGTG

TGCTGGAGACACTGGGAGCGGCGGGCCCCAGGCAAAC

TTGCACGACGCCTGCCAGGGCGATTCGGGAGGCCCCC

TGGTGTGTCTGAACGATGGCCGCATGACTTTGGTGGG

CATCATCAGCTGGGGCCTGGGCTGTGGACAGAAGGAT

GTCCCGGGTGTGTACACAAAGGTTACCAACTACCTAG

ACTGGATTCGTGACAACATGCGACCGTGA.

Another preferred embodiment of the invention relates to a vector containing a DNA sequence according to the invention.

Another preferred embodiment of the invention relates to a vector according to the invention, wherein said DNA sequence is preceeded by a lac promoter and a ribosomal binding site. Suitable vectors according to the invention include, but are not limited to viral vectors such as e.g. Vaccinia, Semliki-Forest-Virus and Adenovirus, phagemid vectors and the like. Preferred are vectors which can be advantageously used in E. coli, but also in any other prokaryotic host such as pPROTet.E, pPROLar.A, members of the pBAD family, pSE family, pQE family and pCAL.

Another preferred embodiment of the invention relates to the vector pComb3HSS containing a DNA according to the invention, wherein the expression of the gp III protein is suppressed or inhibited by deleting the DNA molecule encoding said gp III protein or by a stop codon between the gene coding for a polypeptide containing the kringle 2 domain and the serine protease domain of tissue plasminogen activator protein and the protein III gene.

Another important aspect of the present invention relates to a prokaryotic host cell comprising a DNA molecule according to the invention.

Another important aspect of the present invention relates to a prokaryotic host cell comprising a vector according to the invention.

Another important aspect of the present invention relates to an E. coli host cell comprising a DNA molecule according to the invention.

Another important aspect of the present invention relates to a E. coli host cell comprising a vector according to the invention.

Yet another important aspect of the present invention is the use of a DNA molecule according to the invention or of a vector according to the invention or a host cell according to the invention in a method for the production of a polypeptide having the activity of tissue plasminogen activator.

Yet another important aspect of the present invention is the use according the invention as described above, wherein said method is a method according to the invention.

Another very important aspect is a pharmaceutical composition comprising a substance obtainable by a method according to the invention and pharmaceutically acceptable excipients and carriers. An example for said substance is the K2S molecule described supra. The term "pharmaceutically acceptable carrier" as used herein refers to conventional pharmaceutic excipients or additives used in the pharmaceutical manufacturing art. Such physiologically acceptable compounds include, for example, carbohydrates, such as glucose, sucrose or dextrans, antioxidants, such as ascorbic acid or glutathione, chelating agents, low molecular weight proteins or other stabilizers or excipients (see also e.g. Remington's Pharmaceutical Sciences (1990, 18th ed. Mack Publ., Easton)). Said pharmaceutical composition according to the invention can be advantageously administered intravenously as a bolus, e.g. as a single bolus for 5 to 10 seconds intravenously.

The invention further relates to the use of substances obtainable by a method according to the invention in the manufacture of a medicament in the treatment of stroke, cardiac infarction, acute myocardial infarction, pulmonary embolism, any artery occlusion such as coronary artery occlusion, intracranial artery occlusion (e.g. arteries supplying the brain), peripherally occluded arteries, deep vein thrombosis or related diseases associated with unwanted blood clotting.

The following example is intended to aid the understanding of the invention and should in no way be regarded as limiting the scope of the invention.

EXAMPLES

Example 1

Materials and Methods

Primer Design

In order to amplify a specific part of tPA gene, a pair of primers SK2/174

(SEQ ID NO:22) and ASSP
[5' GAGGAGGAGGTGGCCCAGGCGGCCTCTGAGGGAAACAGTGAC 3']

(SEQ ID NO:23)
[5' GAGGAGGAGCTGGCCGGCCTGGCCCGGTCGCATGTTGTCACG 3']

were synthesized (Life Technologies, Grand Island, N.Y.). These primers were designed based on the human tPA gene retrieved from NCBI databases (g137119). They were synthesized with Sfi I end cloning sites (underlined) in such a way that the reading frame from the ATG of the gpIII gene in phagemid vector, pComb3HSS, will be maintained throughout the inserted sequence.

Another primer set for site-directed mutagenesis was designed to anneal at the sequence situated between K2S gene and gene III in pComb3H-K2S. The sequence of primers with mutation bases (underlined) for generating a new stop codon were msTPA

[5' ACATGCGACCGTGACAGGCCGGCCAG 3']  (SEQ ID NO:24)
                                                and

MASTPA

[5' CTGGCCGGCCTGTCACGGTCGCATGT 3']  (SEQ ID NO:25).

Amplification of K2S gene by PCR. One µg sK2/174 and ASSP primers together with 50 ng of p51-3 template (obtained from Dr. Hiroshi Sasaki, Fujisawa Pharmaceutical, Japan) were suspended in 100 µl PCR mixture. An amount of 2.5 U Taq polymerase (Roche Molecular Biochemicals, Indianapolis, Ind.) was finally added to the solution. The titrated amplification condition was initiated with jump start at 85° C. for 4 min, then denaturation at 95° C. for 50 sec, annealing at 42° C. for 50 sec, extension at 72° C. for 1.5 min. Thirty five rounds were repeatedly performed. The mixture was further incubated at 72° C. for 10 min. The amplified product of 1110 bp was subsequently purified by QIAquick PCR Purification Kit (QIAGEN, Hilden, Germany). The correctness of purified product was confirmed by restriction enzymes.

Construction of phagemid expressing K2S. The purified PCR product of K2S and pComb3HSS phagemid (kindly provided by Dr. Carlos F. Barbas, Scripps Institute, USA) were digested with Sfi I (Roche Molecular Biochemicals, Indianapolis, Ind.) to prepare specific cohesive cloning sites. Four μg of the purified PCR product was digested with 60 U of Sfi I at 50° C. for 18 h. For pComb3HSS, 20 μg of phagemid vectors were treated with 100 U of Sfi I. Digested products of purified PCR product of K2S and pComb3HSS (~3300 bp) were subsequently gel-purified by the QlAquick Gel Extraction Kit (QIAGEN, Hilden, Germany). T4 ligase (Roche Molecular Biochemicals, Indianapolis, Ind.) of 5 U were introduced to the mixture of 0.7 μg of purified Sfi I-digested pComb3HSS and 0.9 μg of purified Sfi I-digested PCR product. Ligation reaction was incubated at 30° C. for 18 h. The newly constructed phagemid was named pComb3H-K2S.

Transformation of E. coli XL-1 Blue. Two hundred μl of CaCl$_2$ competent E. coli XL-1 Blue (Stratagene, La Jolla, Calif.) were transformed with 70 ng of ligated or mutated product. The transformed cells were propagated by spreading on LB agar containing 100 μg/ml ampicillin and 10 μg/ml tetracycline (Sigma, Saint Louis, Mo.). After cultivation at 37° C. for 18 h several antibiotic resistant colonies were selected for plasmid minipreps by using the alkaline lysis method. Each purified plasmid was subjected to Sfi I restriction site analysis. A transformant harboring plasmid with the correct Sfi I restriction site(s) was subsequently propagated for 18 h at 37° C. in 100 ml LB broth with ampicillin 100 μg/ml and tetracycline 10 μg/ml. A plasmid maxiprep was performed using the QIAGEN Plasmid Maxi Kit (QIAGEN, Hilden, Germany). The purified plasmid was reexamined for specific restriction sites by Sfi I and sequenced by AmpliTaq DNA Polymerase Terminator Cycle Sequencing Kit (The Perkin-Elmer Corporation, Forster City, Calif.).

Site-directed mutagenesis of pComb3H-K2S. 10 ng of pComb3H-K2S template were mixed with 125 ng of msTPA and masTPA primers. PfuTurbo DNA polymerase (Stratagene, LA Jolla, Calif.) of 2.5 U was added to the mixture for cycle amplification. The reaction started with one round of 95° C. for 30 sec. Then it was followed by 16 rounds consisting of 95° C. for 30 sec, 55° C. for 1 min, and 68° C. for 9 min. The reaction tube was subsequently placed on ice for 2 min. In order to destroy the template strands, 10 U of Dpn I restriction enzyme (Stratagene, LA Jolla, Calif.) were added to the amplification reaction and incubated for 1 h at 37° C. This synthesized product (MpComb3H-K2S) was further used to transform E. coli XL-1 Blue.

Preparation of phage-display recombinant-K2S. After pComb3H-K2S was transformed to XL-1 Blue, the phage display technique was performed. A clone of pComb3H-K2S transformed E. coli XL-1 Blue was propagated in 10 ml super broth containing ampicillin 100 μg/ml and tetracycline 10 μg/ml at 37° C. until the O.D. [600 nm] of 1.5 was reached. The bacterial culture was subsequently propagated in 100 ml of the same medium and culture for 2 h. An amount of $10^{12}$ pfu of VCSM13 helper phage (Stratagene, La Jolla, Calif.) was used to infect the transformed E. coli XL-1 Blue. After 3 h incubation, kanamycin at a final concentration of 70 μg/ml final concentration was added to culture. The culture was left shaking (200 RPM) for 18 h at 37° C. Bacteriophages which harbored K2S on gpIII (K2S-φ) were then harvested by adding 4% w/v PEG MW 8000 (Sigma, Saint Louis, Mo.) and 3% w/v NaCl. Finally, the harvested phage was resuspended in 2 ml PBS pH 7.4. The phage number was determined by infecting E. coli XL-1 Blue. The colony-forming unit per milliliter (cfu/ml) was calculated as described previously (Lobel, L. I., et al., Endocrinology. 138:1232–1239 (1997)).

Expression of recombinant-K2S in shaker flasks. MpComb3H-K2S transformed E. coli XL-1 Blue was cultivated in 100 ml super broth (3% w/v tryptone, 2% w/v yeast extract and 1% w/v MOPS) at pH 7.0 in the presence of ampicillin (100 μg/ml) at 37° C. until an O.D. [600 nm] of 0.8 was reached. Subsequently, the protein synthesis was induced by 1 mM of IPTG (Promega, Madison, Wis.). The bacteria were further cultured shaking (200 RPM) for 6 h at 30° C. The culture supernatant was collected and precipitated with 55% saturated ammonium sulfate (Soeda, S., et al., Life Sci. 39:1317–1324 (1986)). The precipitate was reconstituted with PBS, pH 7.2, and dialysed in the same buffer solution at 4° C. for 18 h. Periplasmic proteins from bacterial cells were extracted by using a chloroform shock as previously described by Ames et al. (Ames, G. F., et al., J. Bacteriol. 160:1181–1183 (1984)).

Immunoassay quantification of recombinant-K2S. In order to detect r-K2S, solid phase was coated with monoclonal anti-kringle 2 domain (16/B) (generously provided by Dr. Ute Zacharias, Central Institute of Molecular Biology, Berlin-Buch, Germany). The standard ELISA washing and blocking processes were preformed. Fifty μl of $10^{11}$ cfu/ml of K2S-φ or secretory r-K2S were added into each anti-kringle 2 coated well. Antigen-antibody detection was carried out as follows. Either sheep anti-M13 conjugated HRP (Pharmacia Biotech, Uppsala, Sweden) or sheep anti-tPA conjugated HRP (Cedarlane, Ontario, Canada), was added to each reaction well after the washing step. The substrate TMB was subjected to every well and the reaction was finally ceased with $H_2SO_4$ solution after 30 min incubation. The standard melanoma tPA 86/670 (National Institute for Biological Standards and Control, Hertfordshine, UK) was used as positive control.

Amidolytic activity assay. A test kit for the detection of tPA amidolytic activity was purchased from Chromogenix (Molndal, Sweden). The substrate mixture containing plasminogen and S-2251 was used to determine serine protease enzymatic activity. The dilution of $10^{-2}$ of each ammonium precipitated sample was assayed with and without stimulator, human fibrinogen fragments. The assay procedure was according to the COASET t-PA manual.

SDS-PAGE and immunoblotting. The dialysed precipitate-product from culture supernatant was further concentrated 10 fold with centricon 10 (AMICON, Beverly, Mass.). The concentrated sample was subjected to protein separation by SDS-PAGE, 15% resolving gel, in the reducing buffer followed by electroblotting to nitrocellulose. The nitrocellulose was then blocked with 4% skimmed milk for 2 hr. In order to detect r-K2S, a proper dilution of sheep anti-tPA conjugated HRP was applied to the nitrocellulose. The immunoreactive band was visualized by a sensitive detection system, Amplified Opti-4CN kit (BIORAD, Hercules, Calif.).

Copolymerized plasminogen polyacrylamide gel electrophoresis. An 11% resolving polyacrylamide gel was copolymerized with plasminogen and gelatin as previously described by Heussen et al. (Heussen, C. and Dowdle, E. B., Anal. Biochem. 102:196–202 (1980)). The stacking gel was prepared as 4% concentration without plasminogen and gelatin. Electrophoresis was performed at 4° C. at a constant current of 8 mA. The residual SDS in gel slab was removed after gentle shaking at room temperature for 1h in 2.5% Triton X-100. Then the gel slab was incubated in 0.1 M glycine-NaOH, pH 8.3, for 5 h at 37° C. Finally, the gel slab was stained and destained by standard Coomassie brilliant blue (R-250) dying system. The location of the peptide harboring enzymatic activity was not stained by dye in contrast to blue-paint background.

Results

Construction of K2S gene carrying vector. From the vector p51-3 we amplified the kringle 2 plus ther serine protease portion of tPA (Ser$^{174}$ in kringle 2 domain to Pro$^{527}$ in the serine protease) using primers sK2/174 and ASSP. The amplified 1110 bp product was demonstrated by agarose gel electrophoresis (FIG. 1, lane 2) and was inserted into pComb3HSS phagemid by double Sfi I cleavage sites on 5' and 3' ends in the correct reading frame. Thus a new vector, pComb3H-K2S, harboring the K2S was generated. In this vector K2S is flanked upstream by the OmpA signal sequence and downstream by gpIII. The correct insertion of K2S was verified both by restriction analysis with Sfi I (FIG. 2, lane 3), PCR-anaysis (demonstration of a single band at 1110 bp), and DNA sequencing. The schematic diagram of pComb3H-K2S map is given in FIG. 3.

Phage-displayed r-K2S. VCSM13 filamentous phage was used to infect pComb3H-K2S transformed *E. coli* XL-1 Blue, X[K2S]. VCSM13 was propagated and incorporated the K2S-gpIII fusion protein during the viral packaging processes. The harvested recombinant phage (K2S-φ) gave a concentration of 5.4×10$^{11}$ cfu/ml determined by reinfecting *E. coli* XL-1 Blue with PEG-precipitated phages. These recombinant phage particles were verified for the expression of r-K2S by sandwich ELISA. The phage-bound heterologous K2S protein was recognized by the monoclonal anti-kringle 2 antibody (16/B) by using sheep anti-tPA conjugated HRP antibody detection system. The absorbance of this assay was 1.12±0.03 (Table 1). The amount of K2S detectable on 10$^{12}$ phage particles is equal to 336 ng of protein in relation to the standard melanoma tPA. In order to corroborate that K2S-gpIII fusion protein was associated with phage particles, sheep anti-tPA conjugated HRP antibody was substituted by sheep anti-M13 antibody conjugated HRP. This immuno-reaction exhibited an absorbance of 1.89±0.07 (Table 1). In contrast, if the capture antibody was sheep anti-M13 antibody, extremely low K2S was observed with sheep anti-tPA antibody conjugated HRP; the absorbance was only 0.17±0.01 (Table 1). This suggested that only a minority of purified phage particles carried K2S-gpIII fusion protein. VCSM13 prepared from non-transformed XL-1 Blue was used as a negative control.

Construction of MpComb3H-K2S. We generated a stop codon between K2S and gpIII in pComb3H-K2S with the aid of the mutagenic primers (msTPA and masTPA) (FIG. 4). In order to enrich the newly synthesized and mutated MpComb3H-K2S, the cycle amplification mixture was thoroughly digested with Dpn I to degrade the old dam methylated pComb3H-K2S template (Dpn I prefers dam methylated DNA). After transforming of *E. coli* XL-1 Blue with MpComb3H-K2S, a transformant XM[K2S] was selected for further study. As a consequence of bp substitution, one Sfi I cleavage site close to the 3' end of K2S gene was lost after site-directed mutagenesis. A linear version of Sfi I cleaved MpComb3H-K2S was observed at 4319 bp without the appearance of inserted K2S gene fragment (FIG. 5, lane 3). Thus, the K2S gene encoding by MpComb3H-K2S was expressed in non-gpIII fusion form in XM[K2S].

Expression and purification of K2S. K2S expression in XM[K2S] was induced by IPTG. r-K2S was detectable by using ELISA both in the periplasmic space and in the culture supernatant. The amount of the heterologous protein in each preparation was determined by sandwich ELISA and related to the standard tPA. From 100 ml of the bacterial culture in shaker flask with the O.D. [600 nm] of 50, the periplasmic fraction yielded 1.38 μg of r-K2S (approximately 32%) whereas 2.96 μg of r-K2S (approximately 68%) was obtained in the ammonium precipitated culture supernatant. Sandwich ELISA was used to verify the PEG precipitated phage from VCSM13 infected XM[K2S]. No r-K2S captured by monoclonal anti-kringle 2 antibody was detected by anti-M13 conjugated HRP, indicating that K2S is not presented on the phage particles if gpIII is missing.

Amidolytic activity measurement. If serine protease domain is present in the sample, plasminogen will be converted to plasmin. The produced plasmin will further digest the S-2251 substrate to a colour product, p-nitroaniline, which has a maximum absorbance at 405 nm. The specific activity of the recombinant product is in accordance with the absorbance. The fibrinogen-dependent enzymatic activity of each sample i.e. K2S-φ periplasmic r-K2S or culture supernatant r-K2S, was evaluated and compared. Both K2S-φ and periplasmic r-K2S illustrated notably low enzymatic activity, which was below the sensitivity of the test (0.25 IU/ml). The culture supernatant r-K2S gave the fibrinogen-dependent enzymatic activity of 7 IU/ml. Thus, from 100 ml culture we obtained a total of 700 IU enzymatic activity. Without fibrinogen no enzymatic activity of the r-K2S purified from culture supernatant was observed—whereas standard melanoma tPA showed some activity.

Demonstration of recombinant protein by immunoblotting. Partially purified K2S from culture supernatant of XM[K2S] revealed a molecular mass of 39 kDa by using sheep anti-tPA antibodies (FIG. 6). The negative control, partially purified culture supernatant of non-transformed XL1-Blue, contained no reactive band with a similar size.

Localization of active enzyme by PAGE. The plasminogen has been copolymerized and immobilized with gelatin in the polyacrylamide gel prior to electrophoresis. The ammonium sulfate precipitated culture supernatants of *E. coli* XL-1 Blue, *E. coli* XL-1 Blue transformed with pComb3HSS and XM[K2S] were analyzed (FIG. 7). All samples were processed in non-reducing condition to preserve the correct conformation and activity of the serine protease domain. Transparent areas of serine protease digested plasminogen were observed only in the ammonium sulfate precipitated culture supernatants of XM[K2S] at 34 and 37 kDa postions. The other samples gave no clearing zones. The positive control lane of standard melanoma tPA also demonstrated enzymatic activity at 66 and 72 kDa positions.

What is claimed is:

1. An isolated DNA molecule comprising:
   (a) DNA encoding an OmpA signal peptide;
   (b) DNA encoding a tPA or K2S molecule;
   (c) DNA encoding a peptide selected from the group consisting of SEGN (SEQ ID NO:9) and SEGNSD (SEQ ID NO:10);
      wherein said DNA of (a) is located upstream of said DNA of (c), and said DNA of (b) is located downstream of said DNA of (c);
      wherein said DNAs of (a), (b), and (c) are operably linked.

2. The isolated DNA molecule of claim 1, wherein the OmpA signal peptide is encoded by the sequence of SEQ ID NO:3.

3. The isolated DNA molecule of claim 1, wherein said DNA of (c) is TCTGAGGGAAAC (SEQ ID NO:20).

4. The isolated DNA molecule of claim 1, wherein said DNA of (c) is TCTGAGGGAAACAGTGAC (SEQ ID NO:1).

5. The isolated DNA molecule of claim 1, wherein said DNA of (b) is SEQ ID NO:4.

6. The isolated DNA molecule of claim 1, wherein said DNA of (b) encodes a K2S molecule selected from the group consisting of SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

7. The isolated DNA molecule of claim 1, wherein said DNA of (b) encodes amino acids at least 90% identical to amino acids 87–527 of SEQ ID NO:19.

8. The isolated DNA molecule of claim 1, wherein said DNA of (b) encodes amino acids at least 90% identical to amino acids 174–527 of SEQ ID NO:19.

9. The isolated DNA molecule of claim 1, wherein said DNA of (b) encodes amino acids at east 90% identical to amino acids 180–527 of SEQ ID NO:19.

10. The isolated DNA molecule of claim 1, wherein said DNA of (b) encodes amino acids at least 90% identical to amino acids 220–527 of SEQ ID NO:19.

11. The isolated DNA molecule of claim 1, wherein said DNA molecule of (b) hybridizes under stringent conditions to a DNA molecule consisting of SEQ ID NO:4, wherein the hybridization is carried out in 6×SSC, 5×Deinhardt's solution, and 0.1% SDS at 65° C. followed by a washing step in 0.2 SSC, 0.01% SDS at 65° C.

12. A vector comprising the DNA molecule of claim 1.

13. The vector of claim 12, further comprising the DNA sequence of a ribosome binding site and of the lac promoter.

14. The vector of claim 13, further comprising the DNA sequence of the β lactamase gene.

15. The vector of claim 14, further comprising the DNA sequence of the gpIII gene.

16. The vector of claim 15, wherein the expression of the gpIII protein is suppressed or inhibited by deleting the DNA molecule encoding said gpIII protein or by a stop codon between the gene coding for the functional variant of tissue plasminogen activator protein and the gpIII protein.

17. A prokaryotic host cell comprising the DNA molecule of claim 1.

18. The host cell of claim 17, wherein said host cell is *E. coli*.

19. A method of producing a vector comprising inserting the DNA molecule of claim 1, into a vector.

* * * * *